United States Patent [19]
Lynnworth

[11] Patent Number: 5,437,194
[45] Date of Patent: Aug. 1, 1995

[54] ULTRASONIC TRANSDUCER SYSTEM WITH TEMPORAL CROSSTALK ISOLATION

[75] Inventor: Lawrence C. Lynnworth, Waltham, Mass.

[73] Assignee: Panametrics, Inc., Del.

[21] Appl. No.: 206,861

[22] Filed: Mar. 4, 1994

Related U.S. Application Data

[63] Continuation-in-part of Ser. No. 176,930, Jan. 3, 1994, which is a continuation-in-part of Ser. No. 670,702, Mar. 18, 1991, Pat. No. 5,275,060.

[51] Int. Cl.⁶ .................................................. G01F 1/66
[52] U.S. Cl. ................................ 73/861.27; 73/861.29
[58] Field of Search ........... 73/861.31, 861.30, 861.29, 73/861.28, 861.27, 861.26, 861.25

[56] References Cited

U.S. PATENT DOCUMENTS

| | | | |
|---|---|---|---|
| 3,564,912 | 2/1971 | Malone et al. | 73/861.31 |
| 4,024,760 | 5/1977 | Estrada, Jr. | 73/861.31 |
| 4,102,186 | 7/1978 | Brown | 73/861.31 |
| 4,454,767 | 6/1984 | Shinkai et al. | 73/861.31 |
| 4,860,593 | 8/1989 | de Concini | 73/861.31 |
| 5,001,936 | 3/1991 | Baumoel | 73/861.28 |

Primary Examiner—Louis Arana

[57] ABSTRACT

Transducers are mounted in a housing or vessel to propagate signals along a fluid measurement path, and received signals are temporally separated to remove crosstalk in the acoustic propagation paths of interest, which may be paths through the solid body of the housing or vessel or may be separate paths. These may be segments in a closed path circulation or swirl measurement, or different paths carrying combinations of possibly unrelated measurement signals. In a preferred embodiment, a single channel instrument processes signals from plural transducers which are connected in parallel to its processing input, greatly enhancing the effective system bandwidth and reducing equipment costs. Clamp-on circulation measurement or detection systems are described that allow easy evalution and set-up of flow conditioning loops.

16 Claims, 32 Drawing Sheets

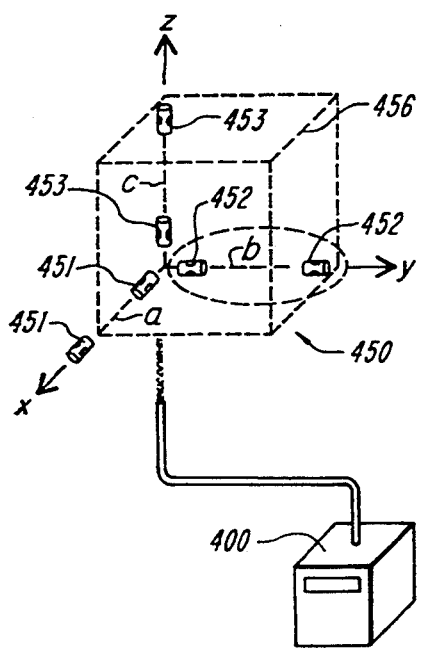
*FIG. 17*
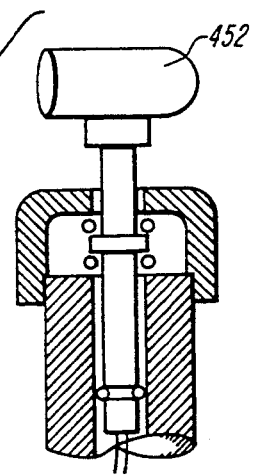
*FIG. 17A*
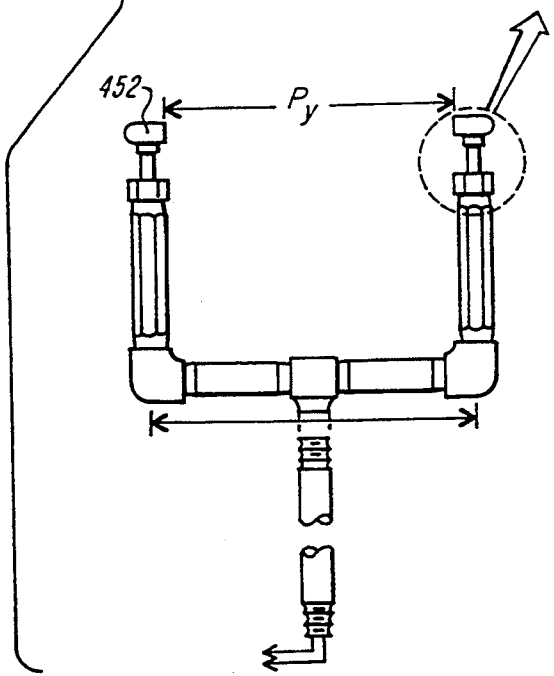

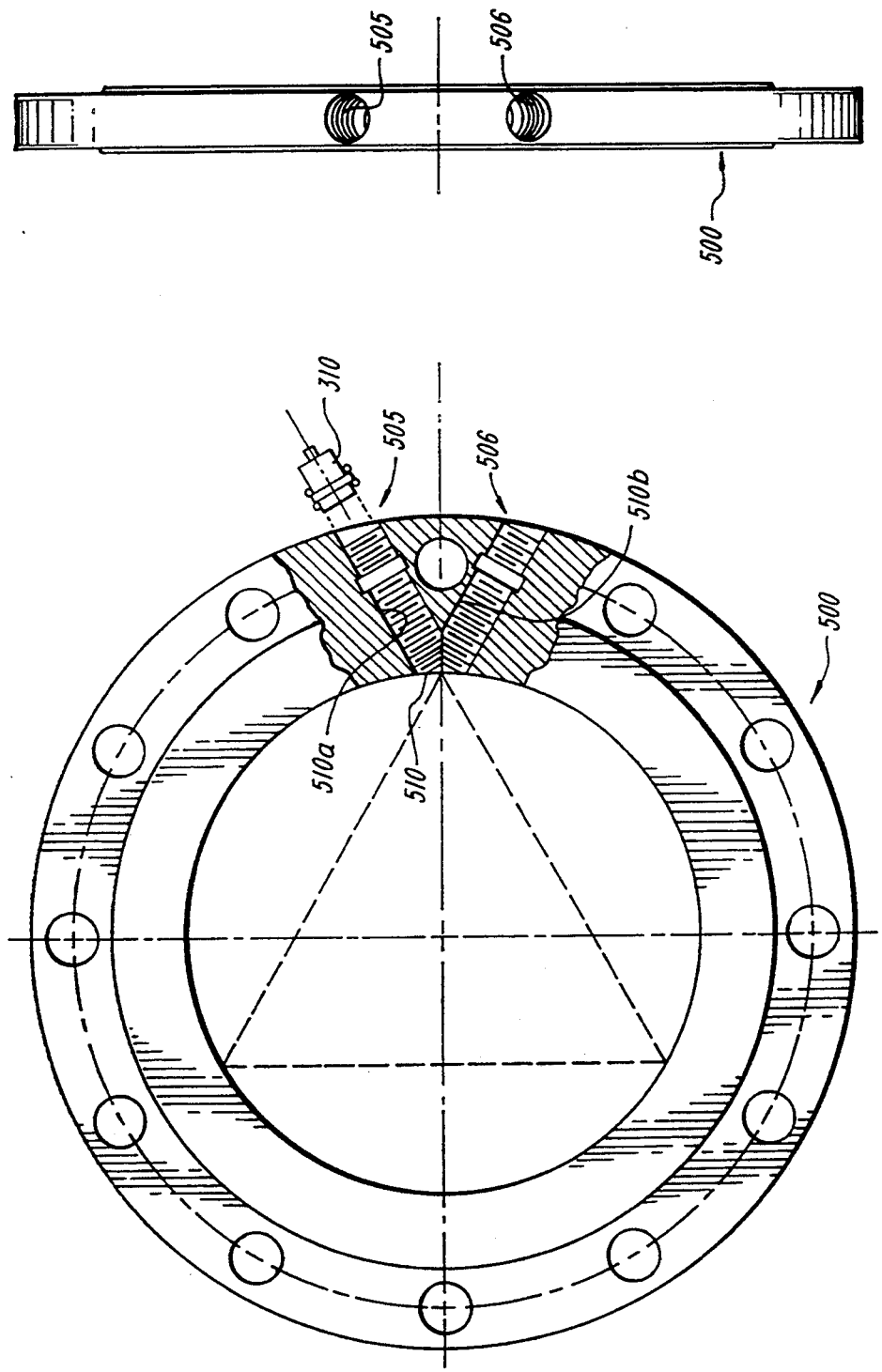

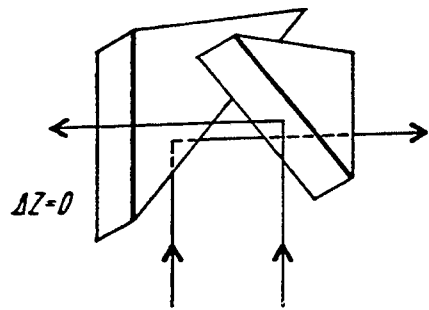
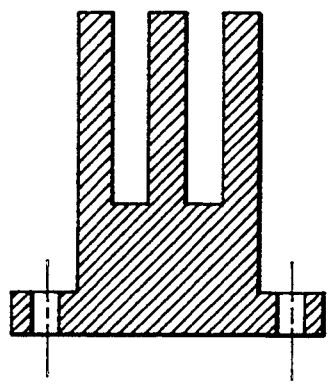
*FIG. 20A*     *FIG. 20B*
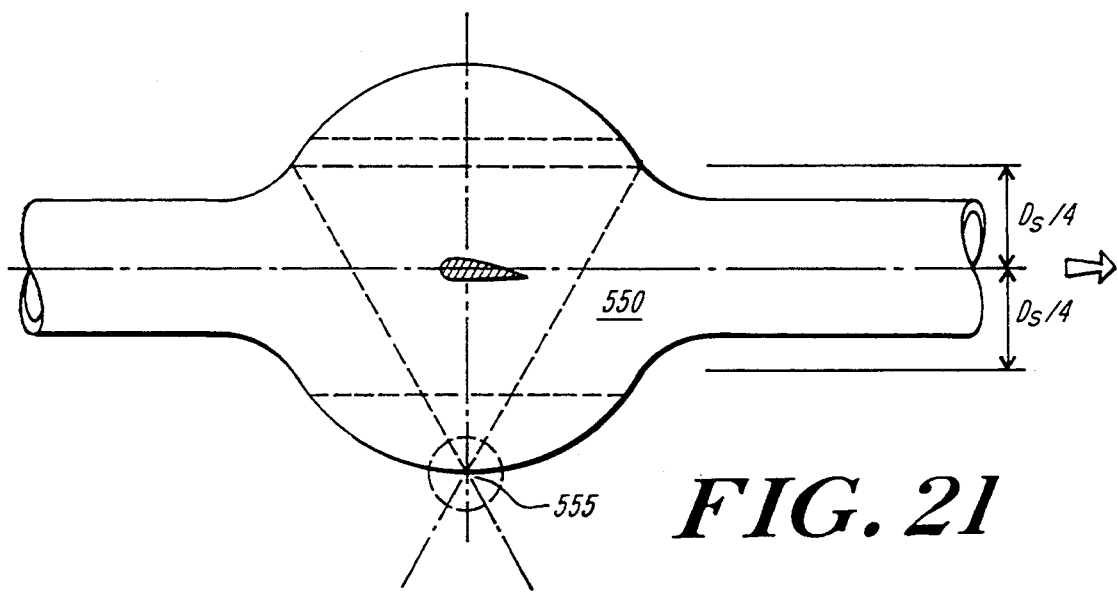
*FIG. 21*
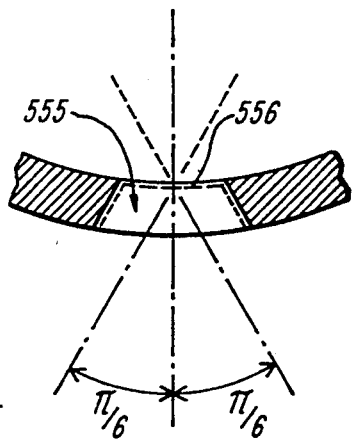
*FIG. 21A*

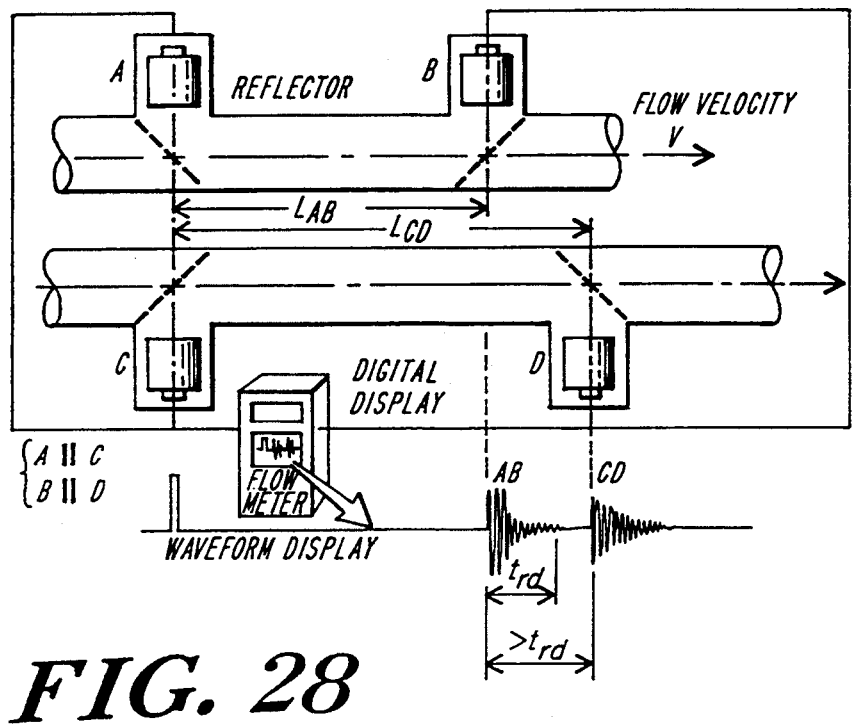
FIG. 28
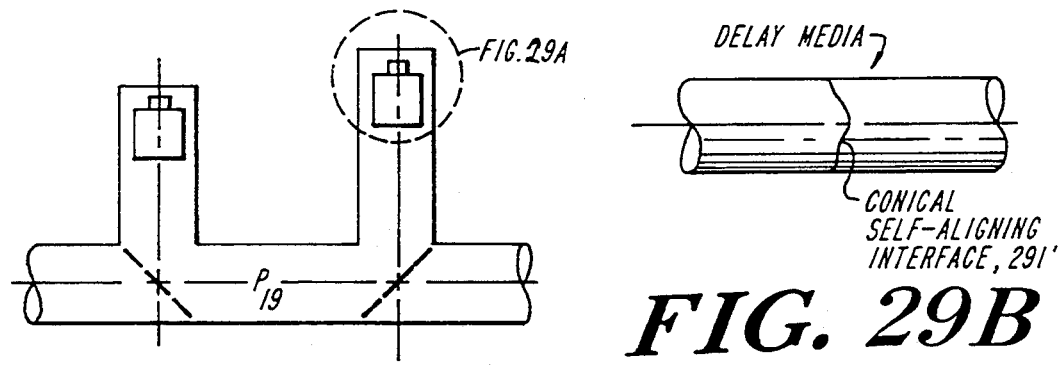
FIG. 29          FIG. 29B
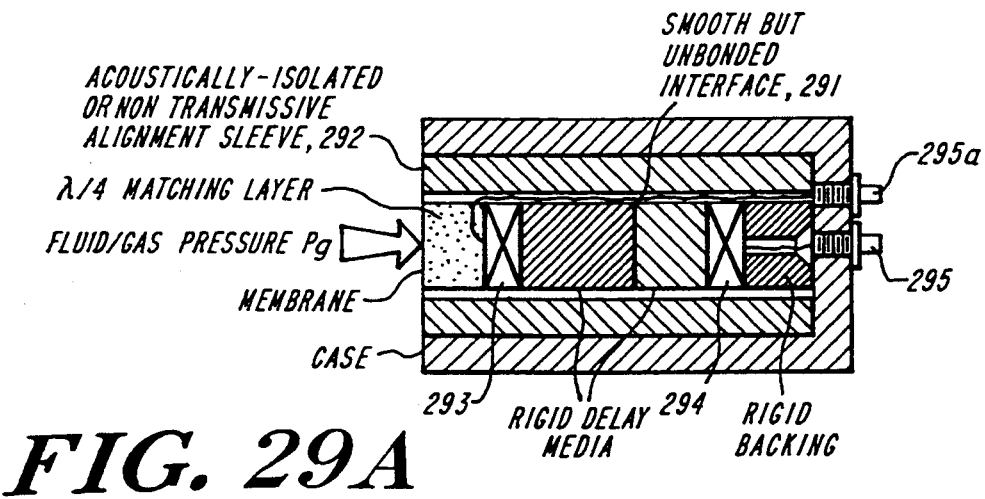
FIG. 29A

ULTRASONIC TRANSDUCER SYSTEM WITH TEMPORAL CROSSTALK ISOLATION

RELATED APPLICATIONS

This application is a continuation-in-part of U.S. Ser. No. 08/176,930, filed Jan. 3, 1994, which was a continuation-in-part of U.S. Ser. No. 670,702, filed Mar. 18, 1991, which issued as U.S. Pat. No. 5,275,060 on Jan. 4, 1994.

BACKGROUND OF THE INVENTION

The present invention relates to ultrasonic transducer and measurement systems of the type wherein an electrically actuated signal source, typically a piezoelectric crystal, is mounted in a mounting assembly fixed to a housing or wedge, or fixed directly to a conduit, to propagate ultrasonic signals through a medium flowing in the conduit. It particularly relates to such transducer and measurement systems wherein the medium has a low density, such as a gaseous medium, or to systems wherein size of the conduit or signal path length through the medium raise considerations of crosstalk.

In these circumstances, the amount of signal energy which can be received through the medium is relatively small or difficult to distinguish. For example, the signal propagates through the gas with a velocity different from and generally much slower than its propagation velocity through the solid structure of the conduit, so it can be difficult to find a suitable timing window in which the received signal can be dependably distinguished from ringing or other energy propagated directly through the conduit walls.

To some extent the problem of signal strength can be addressed by appropriate impedance matching and the use of a large-area diaphragm to couple the crystal to the medium. However, suitable isolation remains a problem, particularly in view of the relatively large amount of energy contained in the solid-path noise band.

One approach to this problem has been discussed in the inventor's U.S. Pat. No. 5,179,860 entitled "Snap-On Flow Measurement System". In that patent, specifically with reference to FIG. 15A thereof, a construction is shown involving acoustically massive rings or a spiral body interposed in the solid body acoustic path between the transmitting and receiving crystals. In applicant's U.S. Pat. No. 5,275,060 entitled "Ultrasonic Transducer System with Crosstalk Isolation", a number of related constructions are shown, in which abrupt impedance changes occur along a path that includes thin-walled conduit, housing, mounting; or stand-off elements. The full disclosure of that latter patent is hereby incorporated by reference herein. The present disclosure is directed to related constructions, further isolation structures, and different practical embodiments of transducer isolation and mounting structures.

BRIEF DESCRIPTION OF THE INVENTION

In accordance with the present invention, a transducer is mounted in a housing or vessel to propagate signals along a fluid interrogation path, and the noise propagation path through the solid body of the housing or vessel is arranged to delay or attenuate transmission of the solid signal, such that in multiple sampling windows, the fluid-transmitted signal is dependably received.

In one embodiment, a base, frame or lattice-work holds sending and receiving transducers in precise alignment to define fluid interrogation paths, while a simple spacer decouples each transducer from the frame. Different path lengths define disjoint reception windows which may be passed in real time by single channel electronics and multiple pairs of transducers may be coupled in parallel to the channel.

In one decoupling embodiment, a specially-configured O-ring mounting is interposed in the solid noise path to attenuate systemic noise. Different constructions utilize this isolation structure, and the transducer elements may themselves be secured by the O-rings, or the elements may be attached to structural members that are secured and isolated by O-rings. Particularly beneficial isolation properties are obtained by lightly sandwiching a mounting flange axially against or between rings of particular attenuating materials. The fluid which is to be sensed may be contained or constrained in a thin walled vessel or conduit, such as a metal foil bellows, which does not itself possess sufficient dimensional stability to define an accurate interrogation path, but forms a suitable flow cell, and which has a wall thickness selected so that signal propagation in the wall is slower than the signal's sound speed in the fluid. A separate holder or framework then precisely positions and supports the transducers and conduit. The bellows provides temporal isolation of the energy burst transmitted directly along the conduit, while the framework provides physical and dimensional rigidity, together with acoustic isolation by extended path, impedance mismatch, attenuating O-ring sandwich or a combination of these techniques. Extremely low impedance conduit materials, such as PVC pipe, may be Used to assure low speed propagation of the solid-borne signal.

Particular systems utilizing O-ring isolators are compact, since the usual stand-offs, dampers and spatial isolators are not required. In particular, many transducers may be mounted on a single hole plug mount to perform multi-path, multi-range or multidirectional ultrasonic interrogation or reflectometry, or multiple transducers may be mounted on arms, lattices or countersunk holes aimed along different axes and effectively isolated from each other. Simple systems consisting of multiple plug-, flange- or frame-mounted transducers may operate in conduits or open regions to provide measurement devices such as a novel anemometer, a device to measure flow, lift or circulation about a structure in a wind tunnel, a system to measure swirl in a conduit, or a single-opening stack or duct gas density or flow meter.

Liquid or gas flow systems using different legs of a thin-walled containment structure, or different length paths in a flowing fluid allow temporal separation of received signals, and include complex multi-measurement systems wherein plural transducers are simultaneously energized to transmit along the paths of different lengths so that energy is received by a second plurality of transducers in several different time windows and two or more of which are processed by a single channel of an instrument.

These and other features of the invention will be understood from the description below, taken together with figures illustrating various embodiments thereof.

BRIEF DESCRIPTION OF THE DRAWINGS

FIGS. 17 and 17A illustrate the transducers of FIG. 15-15D in an unconfined measurement system;

FIGS. 18 and 18A illustrate a flange-mounted single-opening triple midradius path sensor;

FIGS. 20, 20A and 20B illustrate a wind tunnel circulation sensor;

FIGS. 21 and 21A illustrate a chordal circulation sensor in a contoured wind tunnel;

FIG. 28 shows a two conduit electrically paralleled system;

FIGS. 29, 29A and 29B illustrate a pressure sensing flow measurement system and special transducer assembly construction;

DETAILED DESCRIPTION

Figure 1:
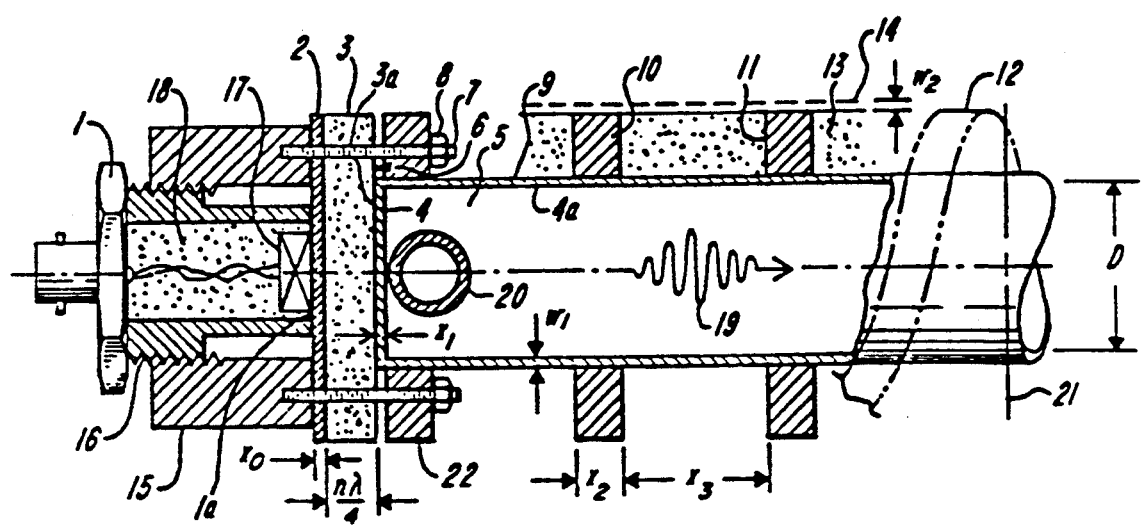
FIG. 1 shows a cross-sectional view of one ultrasonic transducer assembly.

FIG. 1 shows an ultrasonic transducer configuration as described in applicant's aforesaid U.S. Pat No. 5,179,862, the text of which is hereby incorporated by reference for a fuller description of the context and operation of the device. This embodiment has a transducer housing 1 which holds an electroacoustic signal generating element 17 to launch and receive ultrasonic signals indicated by 19.

The wave 19 exits from transducer housing 1 through the housing end window 1a, which may be made of plastic, ceramic or metal foil, via a relatively stiff plate 2 of thickness $x_o$. Plate 2 and housing end window 1a are illustrated as flat but may be slightly curved to simplify coupling or for other reasons. Plate 2, if used in the transducer construction, may be a stainless steel member with its thickness $x_o = 0.05$ to 0.25 mm, for example. It is coupled or bonded to a quarter-wave impedance matcher 3 of thickness $n\lambda/4$, where n is an odd integer and $\lambda$ is the wavelength in the matcher. The wave 19 next passes through a cell end window 4, whose thickness $x_1$ is small compared to wavelength. For example, for a 100 kHz acoustic signal, where the compressional wavelength in stainless steel is about 50 mm, $x_1 \leq 0.1$ mm would be appropriate.

An end window this thin would deform if the cell were evacuated, unless the external atmospheric pressure were prevented from acting against the window, or unless the window were reinforced and stiffened. In FIG. 1 the window is stiffened by bonding the quarter-wave member to it, and also by sealing, as with an O-ring 6. Adapter 15 and plate 2 and matcher 3 are attached to an acoustically-massive ring 22 that is brazed, epoxied or otherwise bonded around the end region of the thin-wall tubular conduit 4a that comprises the major part of the cell 9. The attachment of this ring is accomplished by means of threaded studs 7 and nuts 8, or other conventional means. A gas entry port 20 is located near the inlet of cell 9, and another one, not shown, is symmetrically located near the other end of the symmetrical cell, symmetry being indicated by centerline 21. Gas 5 enters and exits through these ports, and properties of the gas are measured by detection and correlation of acoustic signals passing therethrough.

The speed of sound in most gases is much slower than it is in typical engineering metals like stainless steel, and this may lead to an acoustic short circuit problem, as discussed in the applicant's book, Ultrasonic Measurements for Process Control, Academic press 1989, in chapters 3 and 4. However, if the thickness $w_1$ of wall $4a$ is sufficiently thin (generally $fw_1 >> 1$ MHz.mm) then acoustic energy propagating as a lowest-order asymmetric flexural wave ($A_o$) propagates at a phase velocity $c_f < c_{gas}$. Energy propagating in the $A_o$ mode (as well as energy in other modes) is preferably also attenuated by introduction of a multiplicity of impedance mismatches along the conduit. One structure for this, illustrated in FIG. 1 and described in U.S. Pat. No. 5,275,060 includes acoustically-massive rings 10 and 11, or equivalently, internal thick sleeves (not shown) or an acoustically-massive spiral 12, any of which further serves as a mechanical reinforcement to support the thin conduit wall during evacuation or pressurization. In other embodiments, an internally contacting spiral or sleeves may intercept internal reflected energy and scatter it, thus removing spurious, unwanted (multipath) gas-borne modes and sharpening the axially-transmitted gas-borne ultrasonic signal.

Further attenuation of the unwanted wall-borne energy is accomplished in the device of FIG. 1, by surrounding at least part of the conduit wall $4a$ with dampening material 13. Material 13 may be enclosed by another thin-wall tube 14 of thickness $w_2 >> \lambda$. Soft elastomers such as silicone and fluorosilicone and some urethanes have been found to be effective absorbers for waves near 100 kHz or above. Such materials may also be used as a potting medium 18 within the transducer assembly 1. The spacing $x_3$ between rings 10 and 11, or between spiral turns, is preferably less than the pipe diameter D. The width $x_2$ of the massive rings is preferably on the order of one quarter wavelength of the wave to be blocked. If waves of several frequencies are to be blocked then the inter-ring spacing or dimension $x_2$ ought to be different for different rings; for the spiral embodiment, the pitch or thickness of successive turns of the spiral may vary.

The matcher 3 may be made of Emerson and Cumming syntactic foam, or for temperatures above the rating of such a plastic-based foam, of a low-density or foamy grade of ceramic or graphite. In these examples, the matcher is stiff and capable of supporting pressure differentials. The matcher not only impedance matches but also serves to support the thin window 4. The outside surface of window 4 can also be "wrung" against matcher 3 using a thin layer of oil or other acoustic couplant along interface $3a$. With such a coupling, the window 4 can be maintained flat, yet be removably coupled to the matcher. Plate 2, while thin, can be two to ten times thicker than the window 4 that faces the gas conduit, since plate 2 is on the high impedance part of the circuit, while the window 4 is on the low impedance side.

The housing of transducer assembly 1 may be metallic, e.g., aluminum, stainless steel or titanium, or may be plastic. If plastic, it is preferably shielded electrically on the inside. The housing can also contain a first impedance matching layer (not shown) of impedance $Z_o$ in which case the matcher 3 must have an impedance $Z_3 < Z_o$, as may be inferred from the work of Khuri-Yakub et al (1988) reviewed in applicant's aforementioned book, at page 125.

Figure 1A:
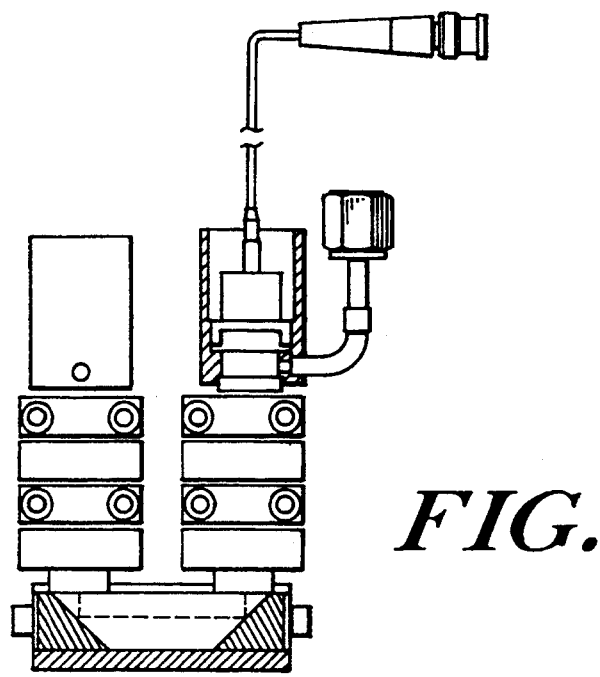
FIGS. 1A and 1B show views of a related assembly.

In the device of FIG. 1, the impedance-varying isolation rings or spiral are placed along the conduit, which thus contains the signal isolation structure, while the transducer housing is devoted to structural or impedance matching elements for launching the acoustic signal into a gas. The principles embodied in FIG. 1 are further illustrated in another assembly. In FIG. 1A, the path of interrogation is folded along a U-shaped channel. The bottom leg of the U-shape is substantially massive and includes two 45 degree reflecting surfaces. The side legs of the U-shape are thin-walled tubing, typically 10 mils or ¼ mm, of SS316, welded at each end into more massive sections. Massive rings are clamped at intervals along the tubing and these collars, corresponding to rings 10 and 11 in FIG. 1, are preferably alternately rotated 90 degrees to stagger their split ring slots and interrupt the thin-wall path as much as possible.

Each transducer assembly in FIG. 1A includes a quarter-wave matcher 3 epoxied directly to the membrane corresponding to 4 in FIG. 1. This holds the membrane in place even under evacuation of the cell. The transducer housing is backed to resist high gas pressure in the cell, equivalent to what is shown in FIG. 1, except that the gland and lock nut are of somewhat different design. A backup seal consisting of an attenuating O-ring of silicone or fluorosilicone may be captured between the transducer housing and the nearby cylindrical wall. In MOCVD (metalorganic chemical vapor deposition) applications, it is common practice to maintain the temperature of cells by immersing them in a water bath whose temperature is kept constant to the order of 0.1 degree C or better. When the cell of FIG. 1A is to be immersed in such a bath, a plastic wrap is used to prevent water from short circuiting the isolation means. This may be shrink wrap.

Figure 2A:
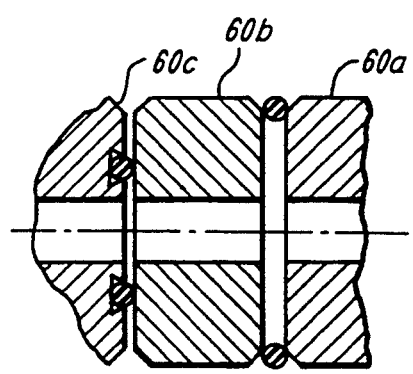
FIG. 2A illustrates a method of ring spacing.
Figure 2:
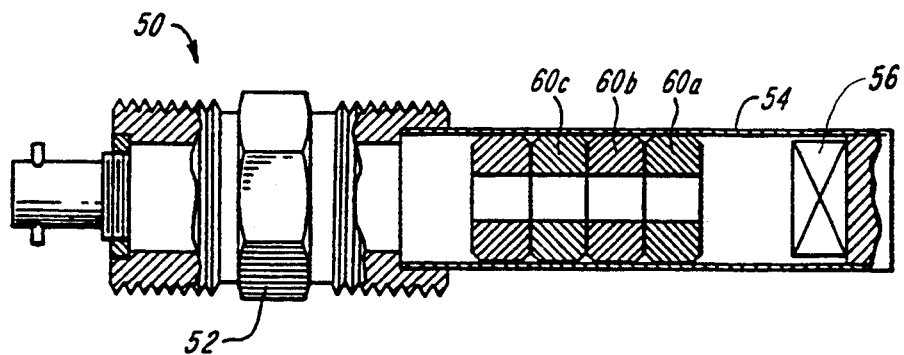
FIG. 2 shows a cross-sectional view of another transducer assembly in accordance with the present invention.

FIG. 2 shows a different embodiment, wherein the transducer housing itself contains the isolation structure.

This transducer assembly 50 includes a threaded base 52 that secures a titanium or stainless steel thin-walled cylindrical housing 54 approximately ten to twenty mils thick, having a signal-transducing crystal 56 mounted at its tip followed by suitable coupling, impedance matching and sealing elements as described in connection with FIG. 1. When the base 52 is screwed into a mounting hole, the crystal end projects into the stack or conduit. Located within the thin-walled transducer housing 54 are a plurality of massive titanium steel or carbon steel rings 60a, 60b, 60c which are press-fit in position spaced apart slightly by interposing silicone O-rings of approximately one sixteenth inch cross section (FIG. 2A). The massive rings may additionally be welded in place. Each ring is chamfered to facilitate insertion, and has an aperture through its center for passage of transducer wires. Each ring is approximately 0.25 to 0.50 inches thick and its edges are chamfered 0.06 inches by 45°. One or more dimples alternatively may be made on each axially-directed face of the inserts, e.g., with a prick punch, and the inserts would then be pressed together so that they actually contact each other at most only at the dimples, and remain essentially acoustically isolated from each other except via the thin walled shell. This assures that the acoustic path between the transducer crystal and the transducer's point of attachment to the stack or conduit passes through an alternating series of massive elements. While four rings are shown, the invention contemplates generally three to six such elements, the number varying with the application and being generally selected based upon considerations of the desired transducer size and weight, allowable insertion loss, and the like, as discussed further below. The gaps between rings may also be configured as shown in FIG. 4.

Figure 3:
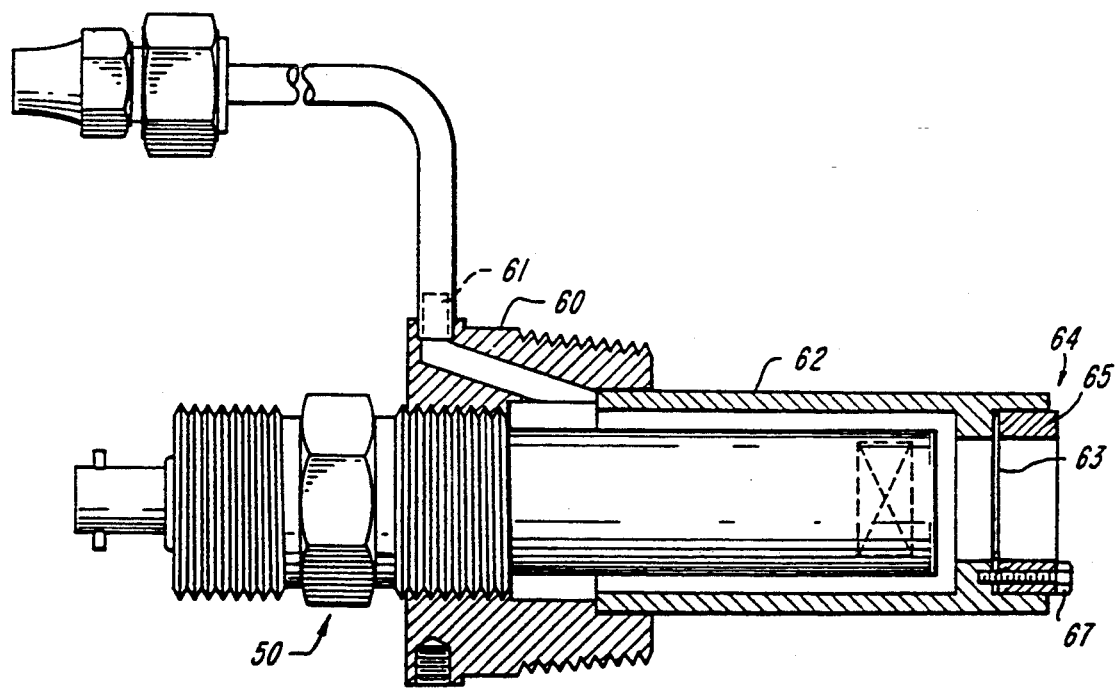
FIG. 3 shows the assembly of FIG. 2 in a high temperature mounting.

FIG. 3 shows the transducer assembly 50 of FIG. 2 mounted for interrogating a flow of stack gas or other high temperature fluid. The previously described sensor structure 50 is mounted within an external mounting assembly comprised of a base 60, and a surrounding sleeve or shell 62 and protective end cap 64, which together define a jacket for a flow of cooling/purge air through passage 61, and via cap 64 into the sensed fluid streams. Cap 64 may include for example, one or more nickel, stainless steel or plated graphite screens 63 secured by a mounting ring 65, which in turn is affixed with cap screws 67. The purge gas may be ambient air or other gas (e.g., $N_2$), may be cooled or heated, and may be directed to flow right over the transducer face, or prevented from doing so and instead be returned to the source area outside the nozzle or stack. Each transducer may have more than one purge line, activated by time, temperature, manual override or signal degradation.

In some installations it is important to be able to remove the transducer assembly without depressurizing the pipe, and without incurring the cost of leaving an "isolation valve" permanently installed at each nozzle. One way of satisfying this requirement is indicated in FIG. 4. Here a nozzle extension 110 is removably attached by means of a removable ball valve 100 (shown in dashed lines to emphasize its non-permanent status) to a nozzle 90 that is welded to the pipe. The nozzle and nozzle extension are coaxially bored through to a diameter $D_R$ and the ball valve has a passageway when open of at least $D_R$. A gland 80 is attached to or is part of the transducer assembly. The gland contains sealing means, illustrated as an o-ring 82 or other packing means, and is installed or removed by connecting an insertion or removal tool to the threads 84 shown at one end, or by other similar mechanical attachment. In the embodiment illustrated, the transducer assembly is installed in a slightly recessed position. Potting material 86 absorbs the ringdown within the transducer's isolation structure. The acoustic masses are coupled to the thin-wall sleeve by circumferential welds, which Applicant has found to constitute a practical joint, fabricable by electron beam welding. Alternatives include brazing or provision of epoxy between the acoustic masses and the surrounding thin-wall sleeve.

Figure 4:
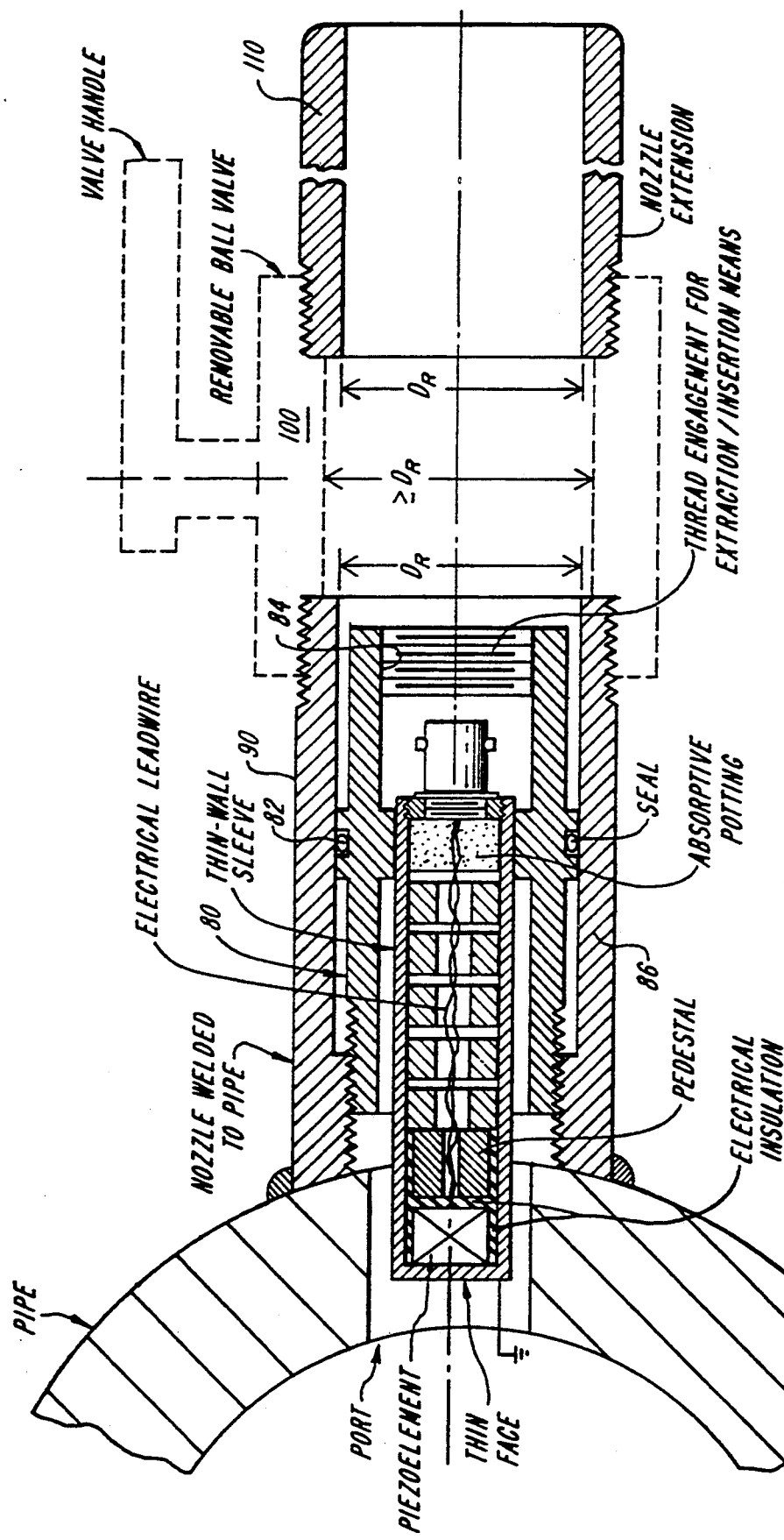
FIG. 4 shows an embodiment of the invention adapted to be removably placed in a valved pipe nozzle.
Figure 5:
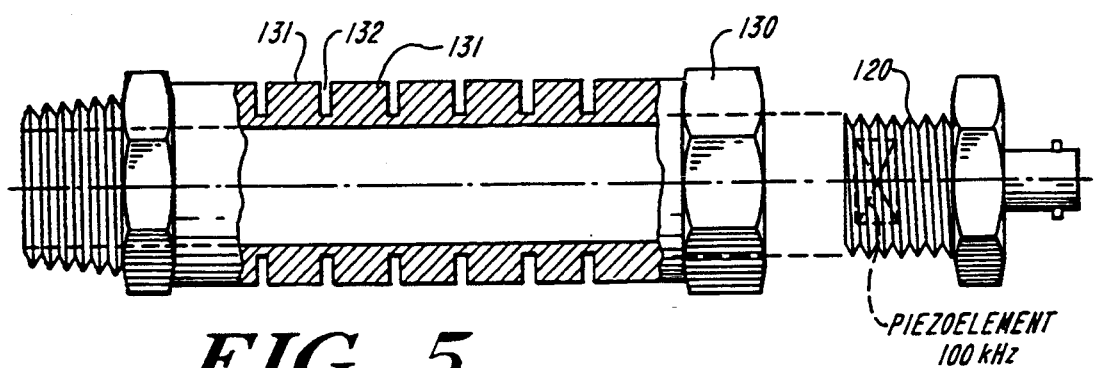
FIGS. 5 and 6 show isolator bodies interposed between a transducer and a conduit.

In the designs of FIGS. 2-4 discussed so far, an isolation structure consisting of alternating hi Z, lo Z (where Z indicates the acoustic impedance) has been permanently built onto the transducer assembly. To facilitate repair of the transducer, and to reduce inventory costs and possibly fabrication costs in some instances, it may be desirable to separate the piezoelectric element from the hi Z, lo Z structure. One way to accomplish such separation of elements is shown in FIG. 5.

Here the transducer housing 120 contains the piezoelectric crystal, mounted against a membrane front face such as a steel membrane of thickness 50 $\mu$m to 250 $\mu$m, which Applicant has found appropriate for frequencies on the order of 100 kHz. As before, a quarter-wave impedance matcher may be installed between the piezo element and the thin window. The transducer housing 120 screws into a separate isolator section 130, and the isolator 130, in turn, screws into the nozzle on the pipe or stack. The isolator specifically includes a multiplicity of impedance mismatches created by alternating acoustic masses 131 and gaps 132. The gaps 132 may be on the outside or inside of the isolator, the former choice being illustrated on FIG. 5. The number of interruptions in the conduit wall that are required to achieve an effective level of attenuation depends on the application, i.e., on the gas impedance and pipe material and geometry. In a very large steel pipe, say one meter in diameter filled with ordinary air, the transit time across the air diameter path at 20 degrees Celsius is about 3 ms. In this amount of time the short circuit or crosstalk decays quite a bit at 100 kHz, and so only a few sections of hi Z, lo Z conduit mismatch are required. But for a small steel pipe, of about 50 mm diameter, the transit time for air at room temperatures is only about 0.05 m/343 m/s = 150 $\mu$s. In this case, about six sections are required, three on each side of the path, to achieve adequate attenuation of the solid-borne noise. These illustrative numerical examples apply for transducers radiating through very thin diaphragms, a construction in which the diaphragms also contribute to the isolation, If thicker windows are used, more isolation is required in the hi Z, lo Z structure.

Figure 6:
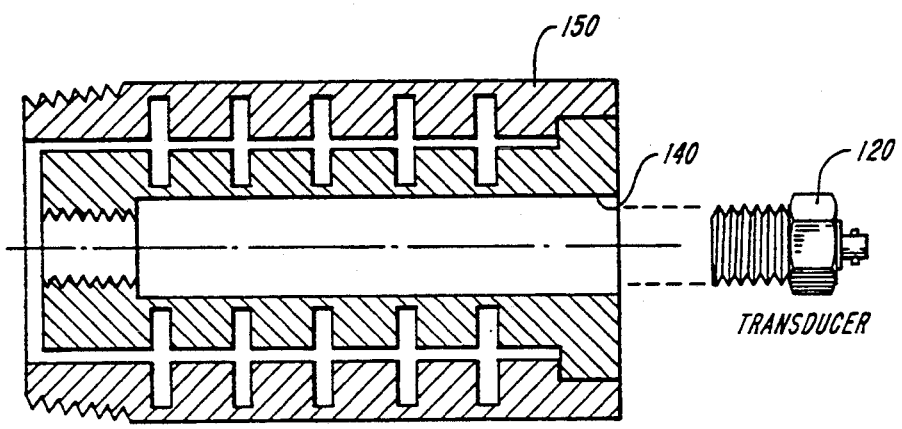

In cases where many sections of hi Z, lo Z appear necessary but where space is restricted in the nozzle's axial direction, a reentrant isolator structure may be employed, as illustrated in FIG. 6. In this embodiment the transducer 120 is mounted at the end of one leg 140 of the isolator structure, and the far end of the other leg 150 attaches to the conduit. Each leg has a structure of alternating impedance mismatches resulting from radially-oriented circumferential slots. As shown, the irregular slotted surfaces of the two legs are essentially enclosed by the legs themselves, rendering the structure largely resistant to clogging accumulations.

Unlike structures of packing washers or the like which have previously been used to isolate transducers, this new structure can be used in a steam environment without waterlogging, deteriorating or changing its properties, and is composed entirely of perfectly elastic, rather than visco-elastic elements.

Viewed as a function of distance along the housing or conduit from the transducer crystal, the acoustic impedance of the isolation structures described herein will be seen to have the profile of a square wave, with a peak-to-valley ratio corresponding to the thickness of the original stock and the depth of the isolating slots 132 (FIG. 5). Preferably this impedance alternation ratio is over 3:1, and more preferably, greater than 6:1.

Figure 7:
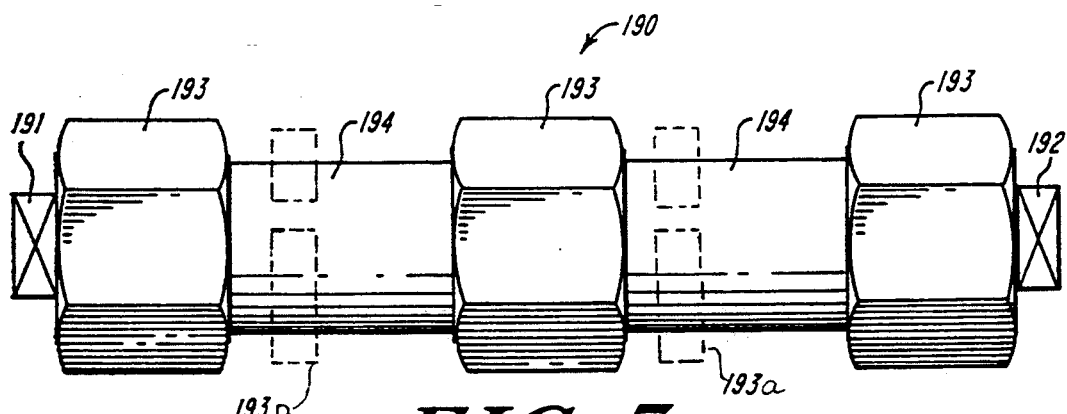
FIGS. 7 and 7A show an isolator body incorporated in a sensing conduit, and show theoretical signal characteristics, respectively.
Figure 7A:
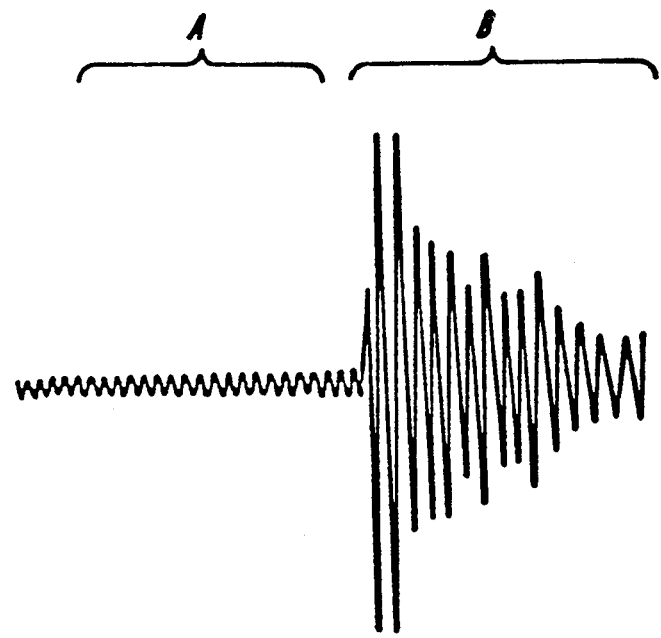
Figure 7B:
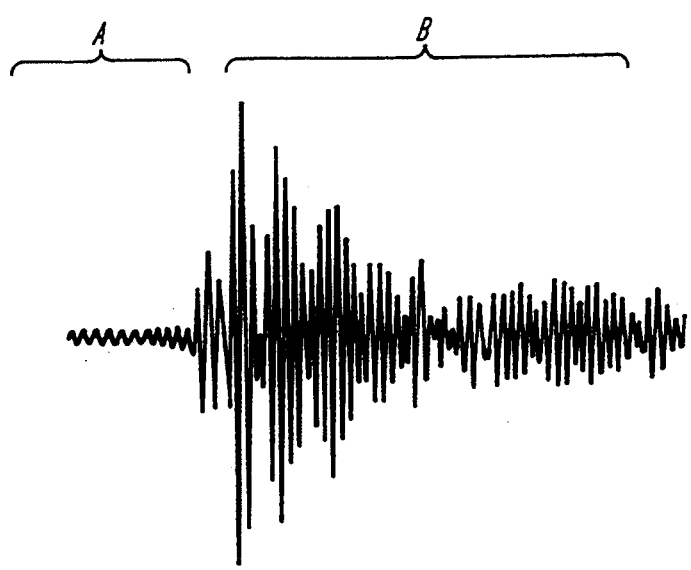
FIG. 7B shows a signal trace for the flow cell of FIG. 1A.

This aspect of the invention may also be implemented using conventional conduits and fittings in a variety of ways. For example, a structure wherein the alternating masses are placed about the conduit between two transducers, rather than between a transducer crystal and the conduit, may be constructed as shown in FIG. 7. In this system 190, a pair of opposed transducers 191,192 launch and receive signals through a fluid path constrained by a conduit formed of alternating segments of 1½ inch high pressure pipe couplings 193 and six inch lengths of pipe 194, the couplings having a much greater wall thickness and acoustic impedance than the pipe lengths. FIG. 7A schematically shows a received signal propagated through air in an imperfect isolator conduit, indicating the level of crosstalk (region A) that, ideally, would be absent, and the gas borne transmitted signal (region B). Depending on gas pressure, the pipes 194 may be thinned and massive collars (shown dashed, 193$a,b$) may be clamped thereto, to achieve SNR (signal to noise ratios) in excess of 100:1. An actual test result for the U-shaped cell of FIG. 1A is shown in FIG. 7B, for which the SNR is on the order of 100:1.

To quantify the nature of impedance mismatch created by the alternating masses and their effect on particular signals, one must deal with the wave impedance, and that means knowing exactly what the wave of interest is, which is to be isolated or blocked by successive mismatches. For many of the frequencies and dimensions of concern here, not just one wave but several are involved, including different modes, e.g., symmetric and asymmetric plate waves. Although one may not know the exact formula for impedance for each wave mode of interest, one can make the assumption that the magnitude of the wave impedance is proportional to the mass per unit area in a plane perpendicular to the axis of the isolator section. This means that one can represent the impedance function like a square wave drawn on a graph of mass per unit area (y-axis) against axial dimension (x-axis). In the "square wave" the peaks and valleys do not need to have equal durations; applicant has found that very small gaps between masses suffice.

Unlike typical impedance mismatches in the prior art of Livengood et al. consisting of alternating materials such as asbestos-like gaskets sandwiched between steel washers, the present case involves lo Z, hi Z steps created by differing amounts of essentially the same materials, typically the same or different metals. This new alternation is amenable to sandwiching masses between concentric thin wall sleeves and thus the lo Z parts are sealable against water or ice and thereby made weatherproof. In contrast, prior-art gasket isolators are subject to being compromised by moisture from weather or other sensed environment, such as steam encountered in steam flowmeters.

Intuitively one might expect that the greater the number or magnitude of Z steps in the square wave, the better the isolator becomes. This turns out to not always be true. In order to optimize the isolator with respect to specific requirements such as minimum weight, minimum length, etc., applicant offers an analysis based on a simple form of the energy transmission equation, $T=4r/(r+1)(r+1)$ where r is the ratio of impedances of the small and large mass sections. A few numerical examples will help explain the optimization found by the applicant, as set forth in the following table, Table I.

TABLE I

| r | T | INSERTION LOSS dB | IL/r dB |
|---|---|---|---|
| 1 | 1 | 0 | 0 |
| 2 |   | .51 | .255 |
| 3 |   | 1.25 | .417 |
| 4 |   | 1.94 | .485 |
| 5 |   | 2.55 | .510 |
| 5.8 |   | 3.00 | .516 |
| 6 |   | 3.10 | .517 |
| 7 |   | 3.59 | .513 |
| 10 |   | 4.81 | .481 |
| 14 |   | 6.04 | .431 |
| 20 |   | 7.41 | .371 |
| 30 |   | 9.04 | .301 |
| 38 |   | 10.00 | .263 |
| 50 |   | 11.14 | .223 |

Table I shows several interesting points. First, as the impedance peak/valley ratio, r, increases, the insertion loss (IL) increases, but not linearly. This is seen from the fact that values of r=6, 14 and 38 yield IL's of approximately 3, 6 and 10 dB, respectively. Second, to get a "useful" insertion loss of at least 3 dB, one requires a value of $r \geq 5.8$. Third, to achieve a particular level of insertion loss it is not immediately apparent whether it is "better" to use a large r or two sections each having half that value of r. For example, r=4 yields more insertion loss that two sections with r=2. Likewise r=6 yields more than two sections of r=3. But r=10 does not yield more than two sections of r=5. This means that if a particular level of IL is required, and if the solution must not exceed a particular weight limit, one cannot simply choose a very large r. It may be necessary to use n sections of an intermediate r value, such that $(n \times IL_0)/(n \times r_0) = IL_0/r_0$ is maximum or near-maximum. The last column of Table I shows that IL/r appears maximized when r is about 6. If other conditions allow it, this choice of r is preferred, because it allows a given IL to be achieved at minimum mass, for IL>3 dB.

It is to be understood that the number of sections may be comprised all in one transducer, shared between two transducers, or shared among transducers and separate "isolator" sections formed in or on a mounting, or about the conduit.

The invention also contemplates the incorporation of isolated transducers directly into equipment other than ducts. For example, the transducers can be installed in valve bodies, preferably upstream from the valve mechanism. The elimination of crosstalk makes it possible for isolated transducers of the present invention to achieve highly accurate measurements in diverse such structures without requiring specially designed flow cells and custom mounting.

Figure 8:
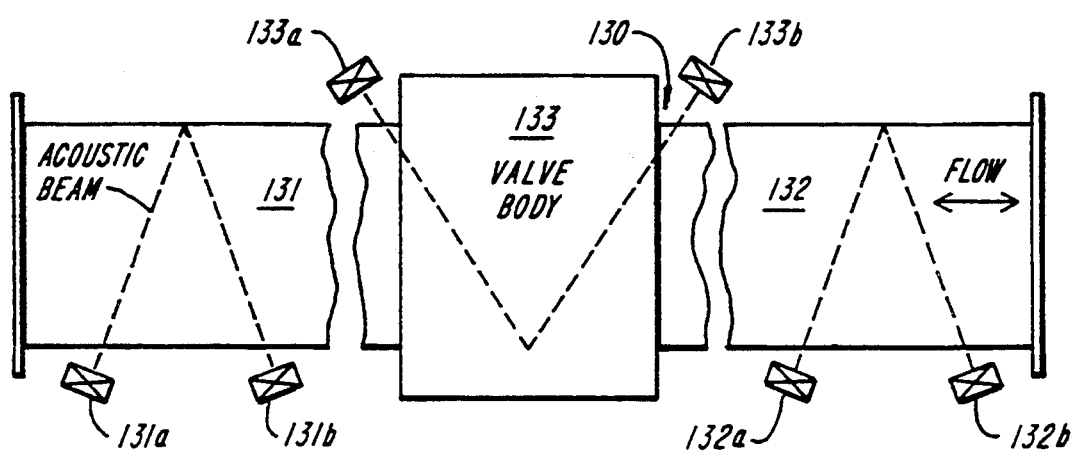
FIG. 8 shows an isolation mounting in a conduit reflected wave system.

FIG. 8 illustrates such a system 130 wherein left and right flow segments 131, 132 lead through a valve body 133, and each segment is provided with a pair of isolated transducers 131*a*, 131*b* or 132*a*, 132*b* for detecting flow in the segment. In this embodiment, bidirectional flow is contemplated, and instrumentation preferably responds to the direction of flow by selecting the pair of transducers which are upstream of the valve body to conduct flow measurements. In cases where minimum length is absolutely necessary, it may be possible to straddle the valve mechanism with a pair of transducers 133*a*, 133*b*. Readings in this case may be possible in only some of the setting positions of the valve mechanism, depending on the extent to which the mechanism interferes with the acoustic beam path between this transducer pair.

Returning now to the constructions of FIGS. 1 and 2 involving a thin diaphragm or window, certain preferred constructions are proposed for reasons of safety to deal with either an occasional or accidental overpressure event in the sensed fluid.

Figure 9:
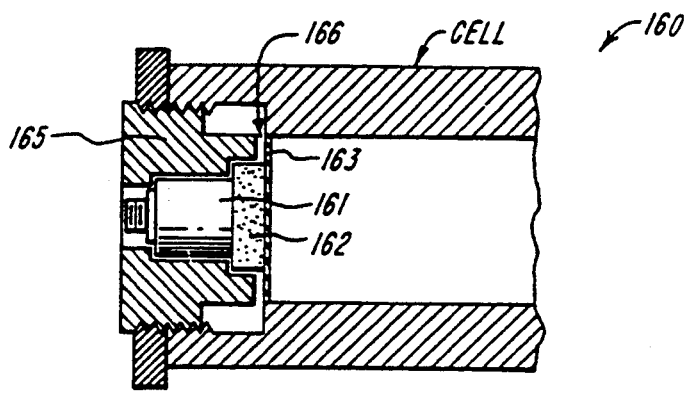
FIGS. 9, 9A show constructions in which transducer coupling to the fluid or housing varies with changing fluid conditions.

In one variation of the transducer mounting, a support is provided that is slightly spaced, by about one mil, from the diaphragm end window. FIG. 9 shows such an embodiment 160, wherein a transducer crystal 161 attaches, via a λ/4 matching block 162, to a diaphragm 163 which normally is spaced one mil from a supporting body 165 at gap 166. Thus, at low pressure in what we may take as normal operating conditions, the support means does not come into play and so does not introduce acoustic crosstalk. In these conditions the gas pressure is so low as to yield only weak ultrasonic signals, the detection of which would be jeopardized by strong crosstalk. But when pressure becomes high, the support 165 limits the motion of the diaphragm to safe excursions by bearing against the diaphragm. In so doing, crosstalk is increased, but at the same time the signal strength increases due to better match between transducer and gas impedance. Hence the signal to noise ratio can still be high enough to allow useful measurements. The effect of residual crosstalk can be reduced by recording it as a function of pressure and/or temperature, and then subtracting the recorded values from the resultant (signal+noise) detected signal. The increased signal, whose amplitude increases nearly in proportion to gas pressure, will be noted later on in sensor configurations that sense gas density or gas pressure.

Figure 9A:
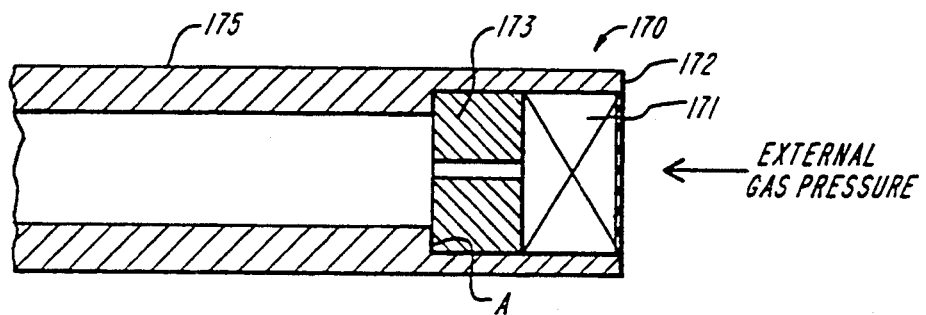

FIG. 9A shows an adaptation of the construction of FIG. 8 to an isolated transducer housing and mount 170. Transducer crystal 171 is coupled to a diaphragm 172 by a couplant, and a pedestal 173 almost spans the cavity between the other side of the crystal 171 and a shoulder of the thin-walled cylindrical isolation section 175 which is for example, similar to that of FIG. 2. As the gas pressure in the sensing chamber to the right of the crystal rises, pressure builds up at shoulder "A", allowing the crosstalk to increase under the high pressure conditions in which adequate signal strength is achieved. The transducer is thus enabled to operate faithfully over a broad range of pressure conditions. In some situations, the crosstalk amplitude may be taken as a measure of gas pressure. This may be understood from prior art work of Crecraft or the applicant, ca. 1964, in which pressure coupling between solids was found to increase approximately in proportion to pressure at least for pressures up to around 1000 psig.

One embodiment of the foregoing construction is especially applicable to a low impedance gas, for example, in aerospace situations where gaseous hydrogen or other gaseous cryogens are involved. In these cases, one of the collateral problems is coupling the piezoelectric element to the window. Bonding sometimes works, but because of differential expansion coefficients it is advantageous to have some degree of flexibility in the couplant. There seem to be so far no really "flexible" couplants known or available to function at temperatures of liquid nitrogen ($-196°$ C.) and below. Applicant has found, however, that the anti-gall compound sold under the trademark Never-Seez [manufactured by Never-Seez Compound Corp., Broadview, Ill.] can be applied between two surfaces at room temperature, squeezed thin and then it couples ultrasound well at room temperature and also at $-196°$ C. Hence this compound can be introduced as a couplant between the crystal and the end window in the isolated transducer designs shown herein, to operate when the application spans all the way down to cryogenic levels. The Never-Seez material, incidentally, was developed for use at high temperatures, over 1000° C. Thus, this one couplant will operate at both extremes of temperature, although its aging characteristics remain to be explored. Applicant has identified a second anti-gall compound, sold under the trade name Permatex, Part No. 133K, made by Loctite of Cleveland, Ohio, which is also normally intended for high temperatures, and this too is useful as a cryogenic couplant that can be applied at room temperature. Other suitable cryocouplants may be found among "anti-gall" lubricating compounds.

Another factor addressed by subsidiary aspects of the invention relates more to high temperature gas flows. When transducers made according to this invention are installed in pipes at temperature extremes, the angle that the transducer axis is to make with the pipe depends in part on whether the objective is to have the sound beam's transit time be influenced by flow, or not be so influenced. To be relatively immune to flow, e.g., to measure density or the like, installation would typically be perpendicular to the pipe axis. But if one wants to measure flow by the contrapropagation method (as described for example in applicant's book, Ultrasonic Measurements for Process Control, Academic Press 1989, chap. 4), the usual method is to install transducers at 45 degrees to the flow axis. However, at temperature extremes, if the transducer is recessed in a nozzle, this creates a still region or refraction wedge where the nozzle port enters the freestream, that can significantly divert the propagation path.

To minimize refraction, applicant recognizes that the angle of incidence should be as near zero as practical. On the other hand, too small an angle means that the small upstream-downstream path component results in a time difference that generally is too small to be measured accurately. Ideally one would like to use normal incidence, thereby avoiding the refracting wedge at temperature extremes, and yet achieve a useful propagation path component L>zero. Applicant has found that at 100 kHz, where commercially available ultrasonic flowmeters such as the Panametrics model GP68 can resolve delta t to 10 ns, a useful minimum delta t is 1 $\mu$s, where delta $t = 2LV/c^2$. (This sensitivity corresponds to flow resolution of 1%.) In large pipes of diameter D>300 mm at high flow velocities, it often turns out that an L of a few centimeters suffices, say L=3 cm=30 mm. Thus L/D may be on the order of 30 mm/300 mm=0.1. Now if the half-angle of the ultrasonic beam in radians measured at the $-3$ dB points exceeds L/D, normal incidence can be used, and the transducers can simply be installed offset by the axial distance L. This simplification is important with respect to safe hot tapping and nozzle attachment, since these installation operations are greatly simplified at normal incidence.

Figure 10:
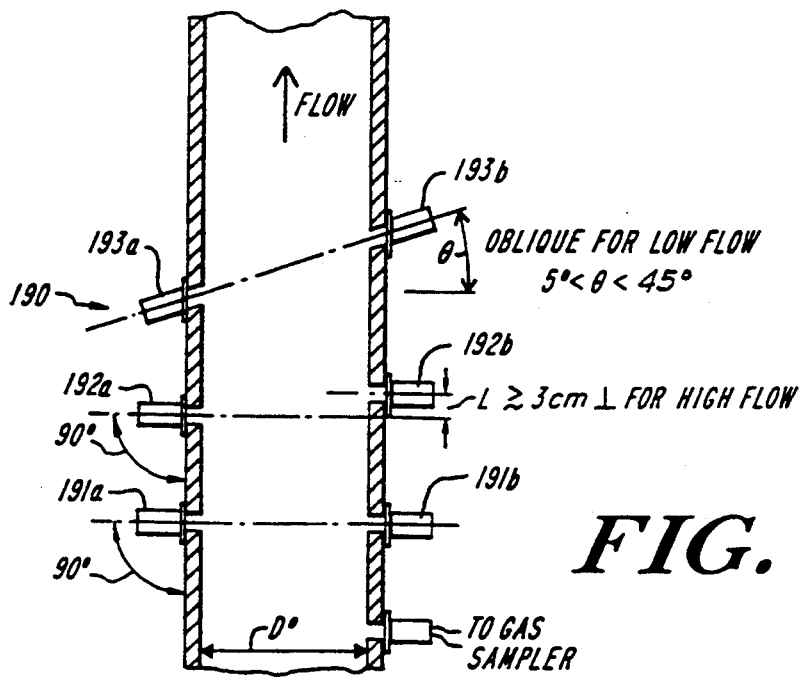
FIG. 10 illustrates slant and offset mounting geometries of transducers in systems according to the present invention.

In cases where both low and high flows can occur, all at high temperature, for example, the invention further contemplates providing multiple sets of ports. As shown in FIG. 10, the ports for high velocity 191*a*, 191*b*, 192*a*, 192*b* can be at normal incidence, while the ones for low velocity can be oblique because at low velocity the refracting wedge is not so distinct since the freestream temperature tends to penetrate into the port.

When using the flow-cooled transducer of FIG. 3 at low flows, the Bernouli effect may not be sufficient to draw cooling air into the free stream and thereby provide self-cooling and self-purging. In other cases air may be a hazardous or disturbing addition to the composition of the measured gas in the stack. In such cases a positive flow of an acceptable, perhaps inert, gas, e.g., pressurized nitrogen, may be introduced as a preferred purge gas.

In still other cases, as where an electric arc is to be extinguished, sulfur hexafluoride may be the preferred purge gas. In one example of such a case, a minimum mass flow of $SF_6$ must be valved into lower-pressure lines, and it is necessary (in one application in which 362 kV and 800 kV double pressure circuit breakers are employed) to ultrasonically verify within 60 ms that the required flow has occurred, or else a safety circuit triggers other more disruptive protective devices. In this application the flow is both transient and turbulent, and it is difficult to measure the flow velocity accurately in so short a time. Applicant proposes to measure such flow indirectly, by instead ultrasonically measuring the temperature change in the gas based on sound speed (as described in applicant's aforesaid book, chap. 5). Here the temperature is measured over one or more paths to obtain a meaningful average temperature, which, integrated over time, provides a measure of the change in gas mass remaining in the supply reservoir. The transducers for such applications where the conduit is already all welded together in an existing plant, are preferably of the clamp-on type. But when such gas conduit systems are designed with ultrasonic interrogation in mind, one can provide for transducers or conduits with the isolated design of the present invention. This is expected to yield higher accuracy than obtainable with clamp-on transducers. In some cases, one transducer can be clamped on, and the other remain "wetted," provided all the necessary isolation can be achieved in the "wetted" transducer or between the two transducers.

Figure 11:
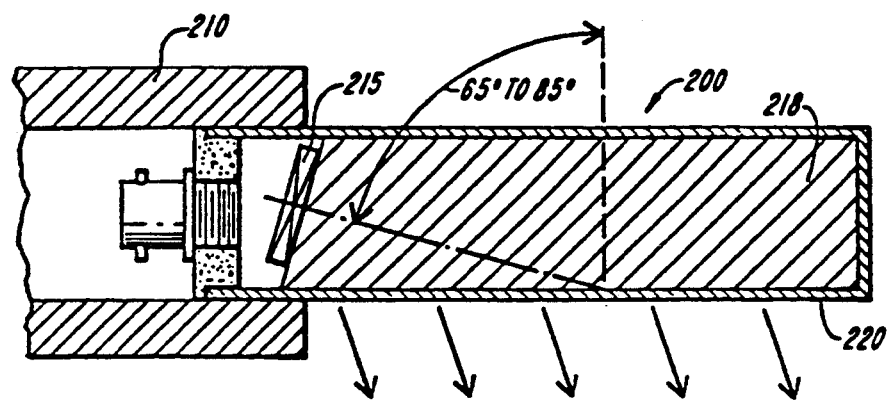
FIG. 11 illustrates a transducer structure for use with low impedance media.

FIG. 11 illustrates another embodiment for an isolation-mounted transducer 200. In this embodiment, an alternating-impedance isolation body 210 is interposed between the transducer crystal 215 and the solid body path of the conduit walls, and the crystal radiates at grazing incidence to excite a thin-walled extended source 220 that radiates or receives the ultrasonic interrogation wave through a surrounding medium. The thin-walled source 220 is thin compared to the wavelength, e.g. preferably under $\lambda/10$ and no more than $\lambda/2$ thick, and is preferably stainless steel containing a wedge 218 made of a low sound-speed material such as CMG or ATJ graphite, or chalcogenide glasses or plastics. The low sound speed contributes to a large refracted angle according to Snell's law. On the other hand if a small refracted angle is sought, then a high sound speed material is preferred, e.g., alumina, beryllia or perhaps beryllium.

Figure 12:
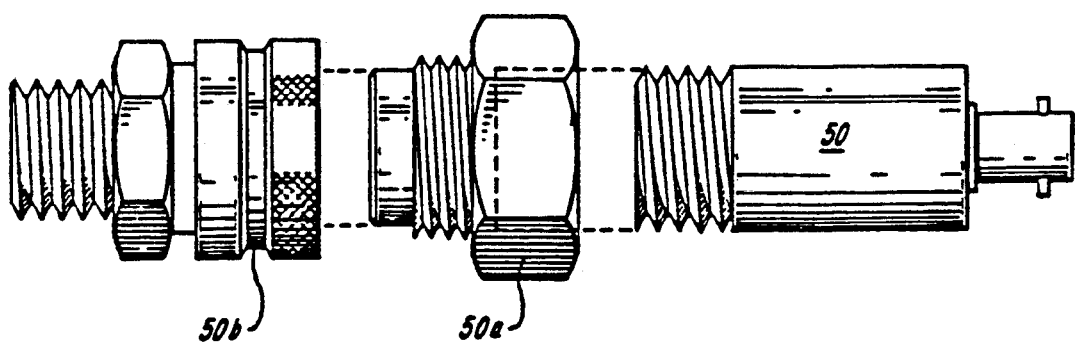
FIG. 12 illustrates a quick-connect embodiment of the invention.

In many of the above-described applications, it is desirable to perform several occasional sets of measurements on a conduit, without any continuing need to monitor fluid parameters, or, as in FIG. 10, one desires to place the transducers at different positions depending on present flow levels. For these applications applicant proposes a conduit-to-transducer mounting as shown in FIG. 12. In this embodiment an isolation-mounted transducer assembly 50 is provided with a quick-disconnect stem fitting 50a, and a corresponding quick-disconnect body 50b is fitted to the conduit or reservoir wall. Suitable interconnecting body and stem parts are, for example, are Swagelok fittings SS-QF-12-B-12-PM and SS-QF-12-S-12-PF. For lower pressure applications, the transducer assembly need not be provided with such secure pressure fittings, and the corresponding mounting may comprise simply a precision bored nozzle and closely fitted cylindrical transducer body which is simply placed in the nozzle bore and positioned or retained by a spring-loaded ball detent. The quick-connect may have an automatic shut-off, or alternatively a plug may be used when the transducer is out.

The foregoing examples illustrate solid body attenuators in which elastic elements—alternate metal rings and thin shells in series—attenuate noise transmission.

It is also possible to provide a relatively simple isolation structure in which O-rings made of attenuating material are lightly sandwiched with low contact force about a steel or highly elastic flange or even a strong plastic solid body. Furthermore, hybrid constructions are possible wherein a conduit or gas measurement chamber is formed of a very thin and structurally indefinite wall—for example a metal bellows—while a separate frame or outer housing provides dimensional precision and structural rigidity to secure the transducers in defined positions. Each of these constructions will be further discussed below.

Figure 13:
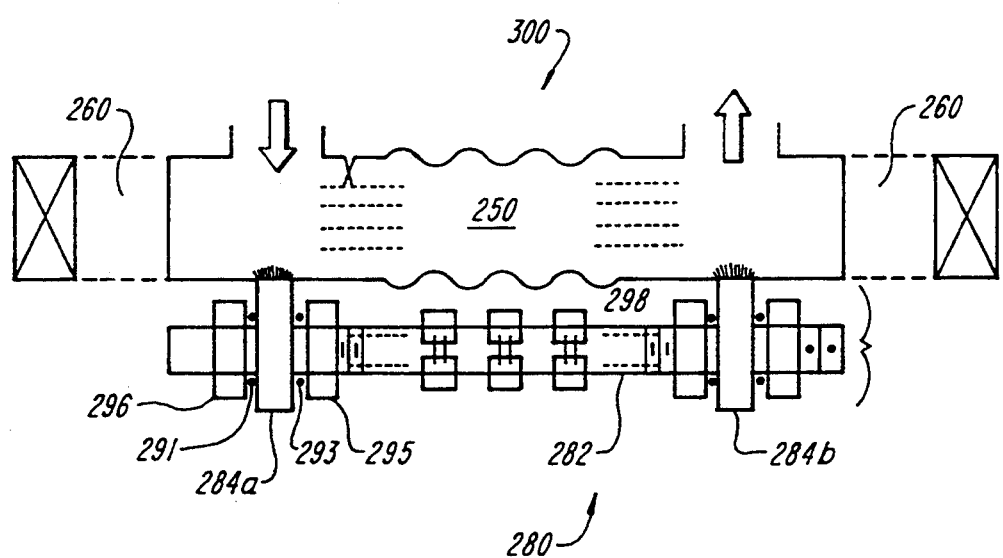
FIGS. 13 and 14 illustrate hybrid systems with separate acoustic and structural isolation sections.

FIG. 13 shows a hybrid system 300 comprised of two major elements, a thin walled containment vessel 250 and a rigid frame 280. Frame 280 consists of a first yoke 284a fitted to one end of the vessel 250, and a second yoke 284b fitted to the other end of vessel 250, with the two yokes being rigidly spaced apart by an elongated rail or body 282. A transducer 260 is fitted into each yoke and directed along the axis of the containment vessel 250. Vessel 250 is a limp and flexible tube, preferably corrugated, and having a very thin wall such that the product of its thickness with the signal frequency (corresponding to the lowest order flexural wave ($a_o$) speed in the material) is low, e.g., below 1 MHz.mm. This assures that the noise in vessel 250 travels more slowly than the gas-carried signal, so that the gas measurement signal may be detected vessel-borne noise arrived As illustrated in FIG. 13, each of the solid frame members constituting a yoke 284a, 284b is secured to the rail 282 by being clamped between a first and second O-ring 291,293, with rigid plates or collars 295,296 tightened against them to securely fix the position of the yoke. The corrugated bellows 250 is rigidly attached to the yoke at each end, preferably by brazing or with a sealing ferrule, gasket or sealing material. Suitable flexible tube assemblies are available from The Cajon Company, a division of The Swagelok Company, of Macedonia, Ohio as their 321SS flexible stainless steel tubing, and are available with glass or weldable metal end fittings (cuffs). These bellows are suitable for relatively low pressure gas measurement applications. Preferably a system for general use in the chemical process industries and for many metalorganic chemical vapor deposition processes would utilize a bellows or corrugated tube of 316 stainless steel, rather than the common commercial 321SS product.

The selection of O-ring material requires some care. Preferably the O-rings are formed of material which is acoustically attenuating and suitable for the intended chemical and thermal environment. Applicant has found silicone, fluorosilicone, neoprene and Buna-N to be suitable materials, with fluorosilicones offering excellent resistance to high temperatures and hydrocarbons. Several common O-ring materials, notably Teflon and Viton, were found to provide very poor isolation and to be unsuitable. The O-ring thickness also requires careful selection. For example, on the assembly of FIG. 13, with O-rings fitted about a ten millimeter diameter rod 282, a silicone O-ring 2.3 mm thick provided best isolation, whereas a ring twice as thick of Neoprene or Buna-N was required. In each case, the ring was tightened adequately to obtain rigidity, but to a less compressed state than is customary when O-rings are used for sealing. For example, a compression of well under forty percent, and preferably about ten percent is suitable, with care being taken that the solid frame 284 and mounting plates 295,296 do not contact each other. A thin wire or protrusion may be brazed to the surface of the plates 295, 296 to act as limit stops. Other isolation means as described above are also shown applied to the rail 282 to further cut down on acoustic short circuiting. For example, as shown in the embodiment of FIG. 13, a plurality of massive damping rings 298 are spaced along the rail 282.

Figure 14:
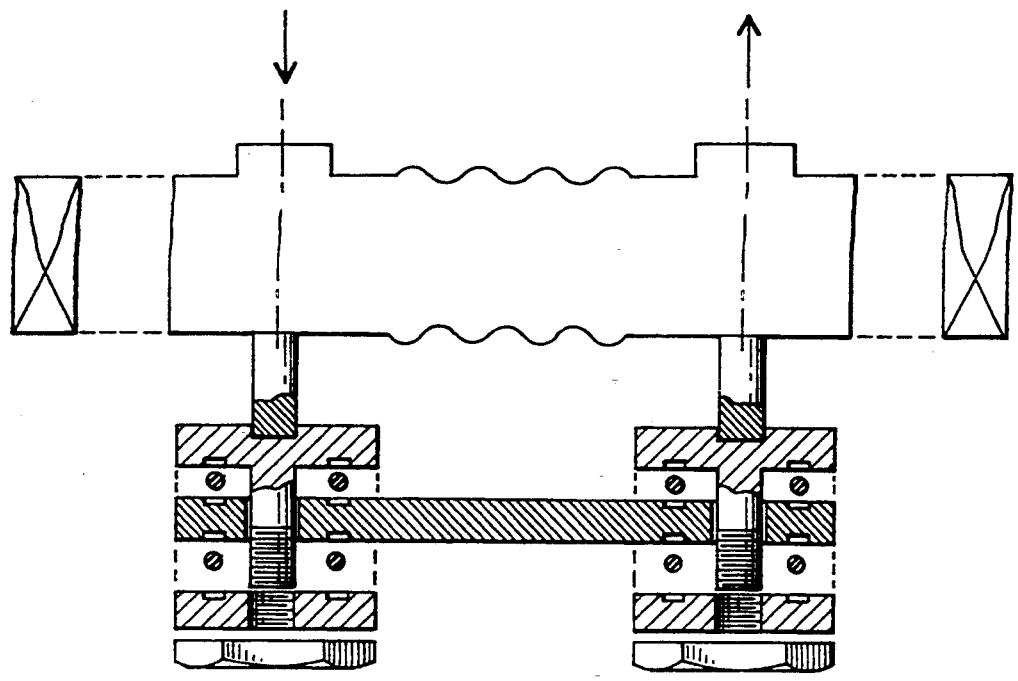

FIG. 14 shows a related O-ring isolation construction in which a dimensionally stable mounting plate is isolated by O-rings from a pair of end posts that hold the bellows.

As was the case with the massive damping rings, this O-ring isolation structure may also be applied directly to the transducers.

Figure 15:
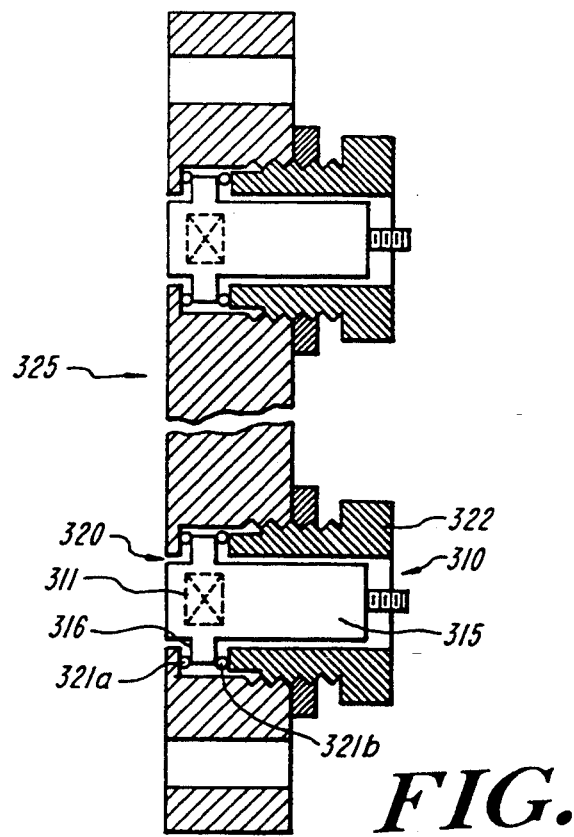
FIG. 15 illustrates transducer isolation with an O-ring sandwiched flange.

FIG. 15 shows such a construction, wherein a transducer including a crystal 311 and suitable coupling and diaphragm are mounted in a small cartridge-like housing or case 315 having a flange 16. The case 315 is fitted into a bore 320 in a conduit or chamber, with the flange sandwiched between a pair of O-rings 321a, 321b. A gland or packing nut 322 tightens the assembly down, allowing secure fixation and slight positional adjustment along the transducer axis. In this manner the transducer itself is isolated from the solid body of the fluid-containing structure. As shown in this illustration, this isolation mount is particularly compact, allowing two or more transducers to be placed adjacent to each other in separate bores in a single solid body 325, which may, for example be the wall of a thick-walled pipe, a plug, or a pipe flange or flange cover as illustrated. The lock nuts, if used, are tightened after the gland is tightened.

Figure 15A:
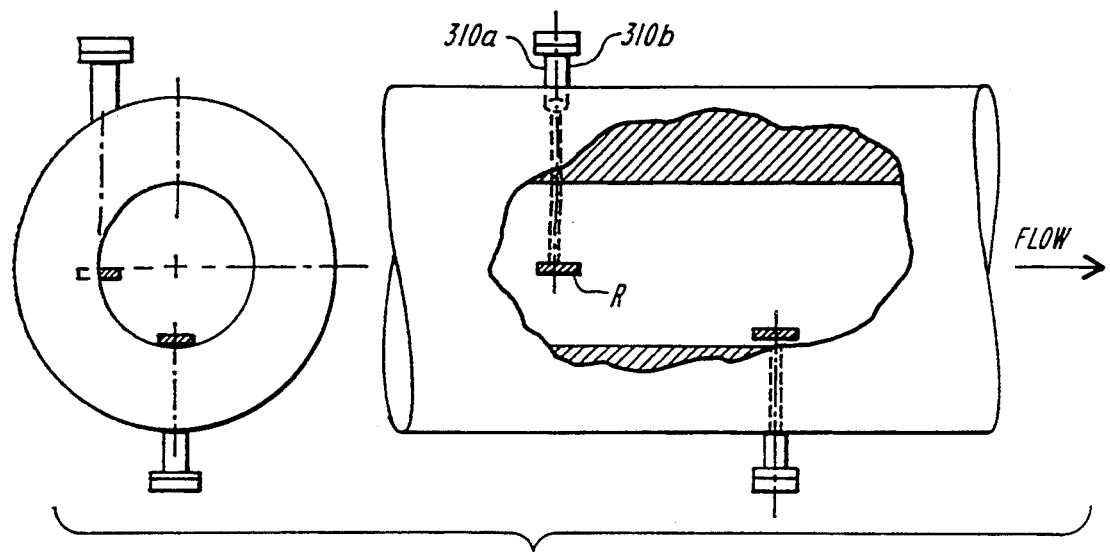
FIGS. 15A-15D illustrate systems using O-ring isolation.

The illustrated bores 320 are shown at normal incidence. Advantageously, applicant has found that with the degree of acoustic isolation provided by this O-ring mounting, sufficiently well-defined signals are obtained to take flow measurements in fluids such as gases in various ducts or conduits that are known in the trade as vents, pipes, headers and stacks, by using transducers spaced apart at a distance L appreciably smaller than the stack or conduit diameter, and mounted at normal or near-normal incidence on a plug or cap. For example, using a small reflector R in the stack or conduit as shown in FIG. 15A a downstream transducer 310b may catch the reflected signal transmitted by an upstream transducer, 310a, both mounted at normal incidence in a single plug or corner plate of small dimension. In smaller conduits the transducers may be mounted in separate bores directly in the conduit wall, or in a single clamp-on mounting block positioned over a wall opening or over a thinned wall position, while remaining substantially isolated from each other. In preferred one-port installations, the measurement of flow averaged over an interrogation path out to the reflector and back, would very nearly equal the area averaged flow velocity in the conduit and would be relatively insensitive to Reynolds Number Re at least for fully developed turbulent flow profiles. The examples in FIG. 15A have this property.

Figure 15B:
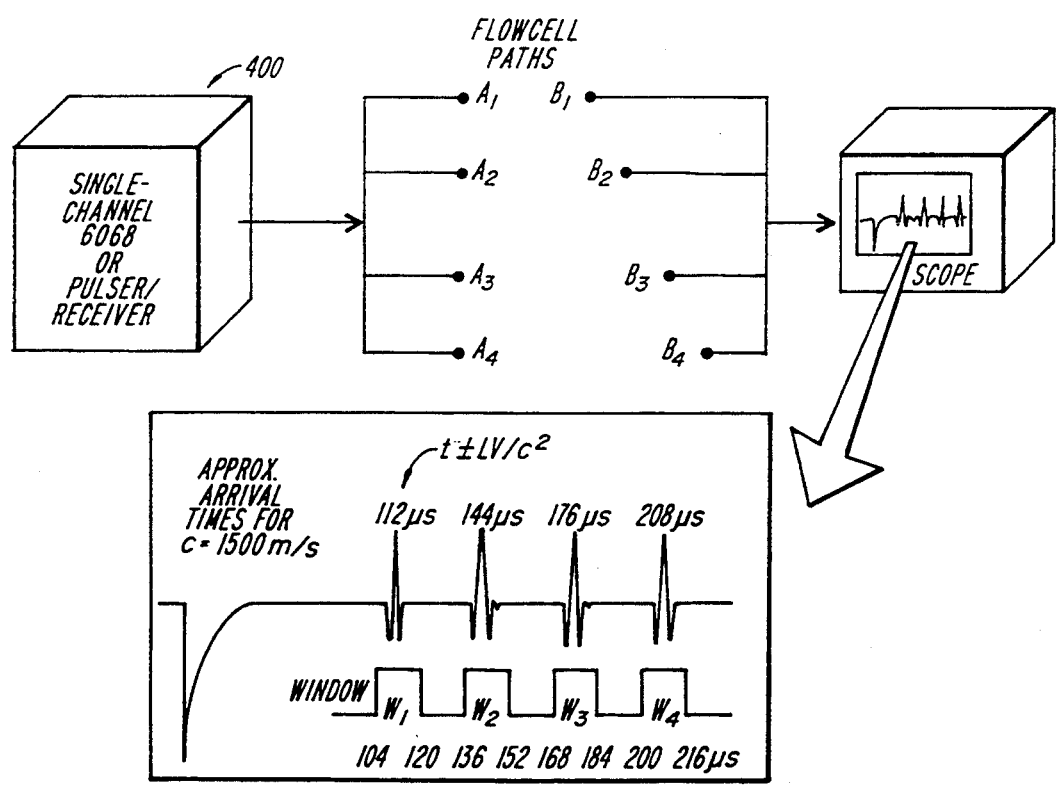

More complex arrangements of transducers in a single conduit, or with a single measurement instrument are thus possible. For example, as illustrated in FIG. 15B, each channel of a four-channel driver/intervalometer measuring instrument 400 such as a Panametrics Model 6068 or GP68 may be attached, without switching, to each of the four sending and receiving transducers ($A_1$–$A_4$ and $B_1$–$B_4$) in four pipes, with the transducers in each pipe arranged to provide four different length paths with the transit time differences each greater than the ring-down time, so that the signals may be received in different time intervals in a single channel from each path of a given pipe with the transducers connected in parallel. Further systems of this type are discussed below, in connection with FIGS. 23–34.

Figure 15C:
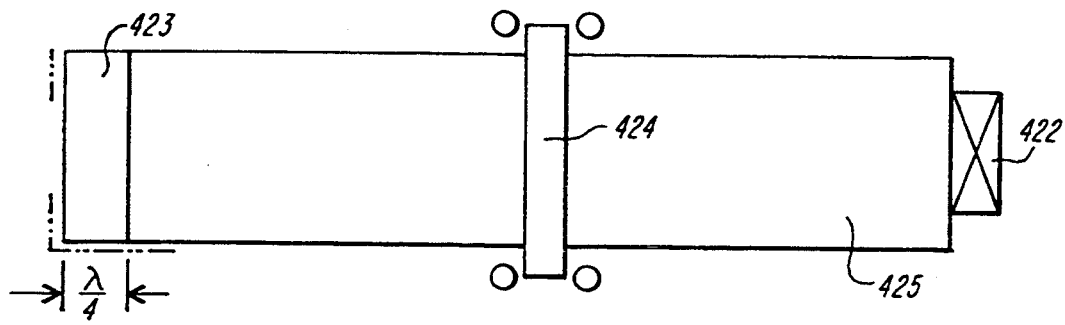

This O-ring isolation mounting is versatile, and in addition to use in a crystal housing or a rigidizing external frame as discussed above, may be applied to a buffer rod or standoff located between a transducer crystal and an impedance matching launching structure for gas interrogation. FIG. 15C shows such a configuration, wherein a transducer crystal 422 is coupled by a buffer rod 425 to a quarter wave coupling block 423, and a flange 424 located at approximately the rod's center of gravity is provided for isolation mounting between O-rings. This allows the crystal to be supported in relative thermal isolation as well as acoustic isolation, many wavelengths, and up to five or more pipe diameters, away from the conduit and fluid.

Figure 15D:
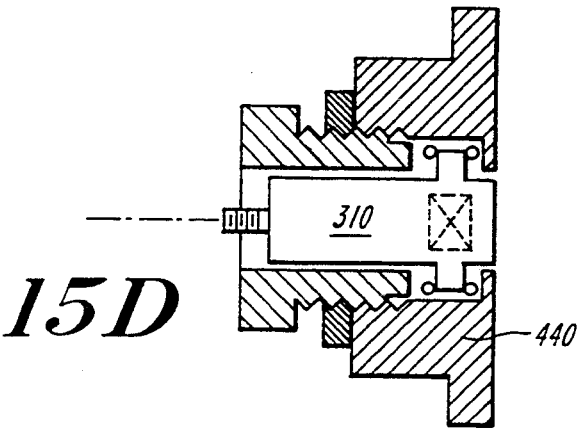
Figure 15E:
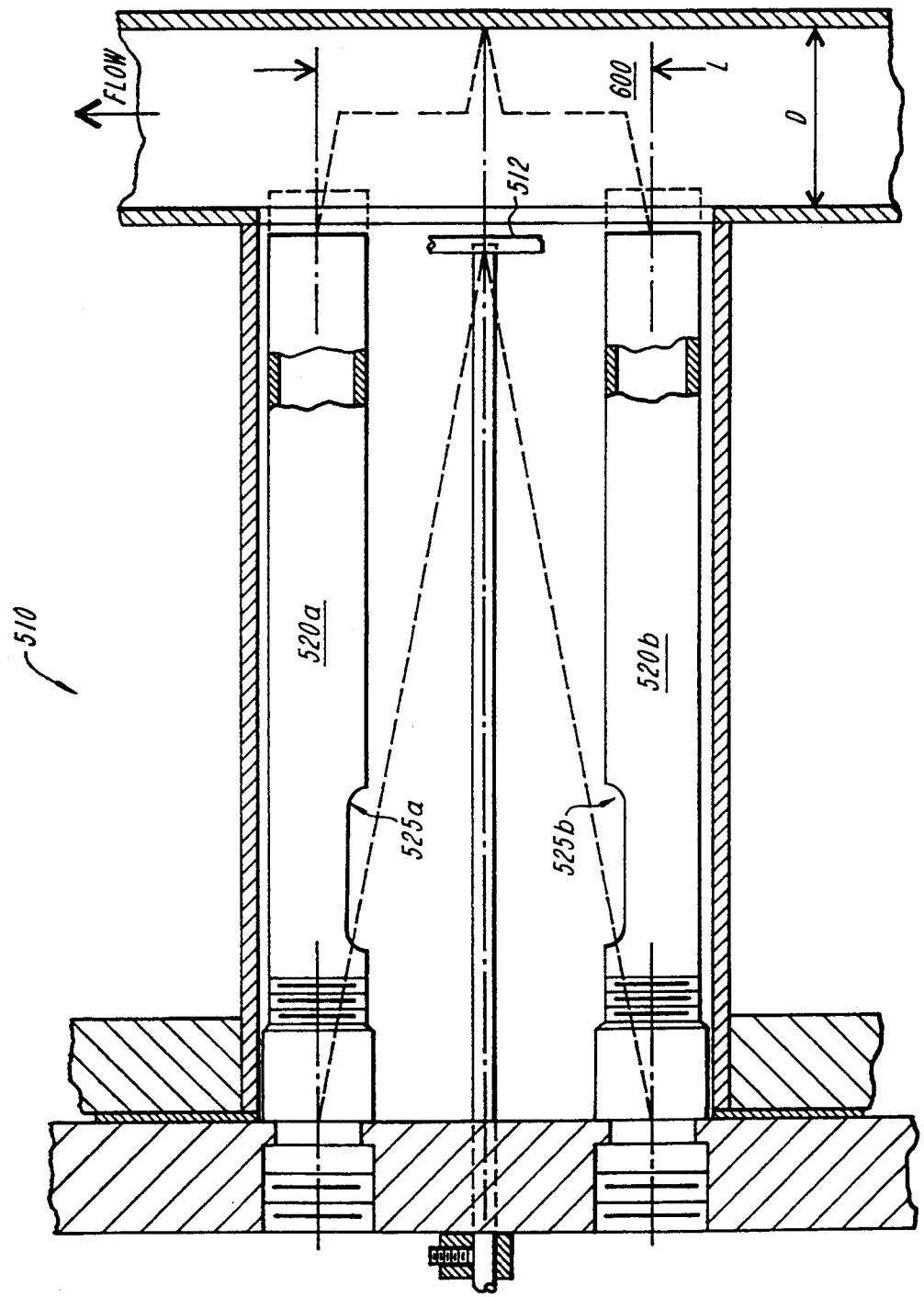
FIG. 15E illustrates a self-referencing one-port system using transducer isolation.

In FIG. 15E there is shown another one-port nozzle assembly 510, similar in some respects to that shown in FIG. 15A for interrogation perpendicular to a conduit, duct or stack. In FIG. 15E, however, there is a reference reflector 512 adjustably positioned very near the inside surface of the duct 600 in which flow is to be measured. This reflector provides a reference echo whose transit time provides a correction to transit times in the freestream across the duct, as is increasingly important if temperature gradients are present. The reference echo amplitude is proportional to the gas acoustic impedance, as mentioned elsewhere herein, and so can be processed to yield gas pressure or gas density. The amplitude of this echo in other circumstances can be used to monitor the cleanliness and integrity of the transducer system. FIG. 15E also shows two waveguiding tubes or pipes 520a, 520b, each concentric with the axis of its respective transducer, and extending essentially to the freestream. This construction avoids beamspread in the nozzle and also avoids most of the turbulence that might otherwise attenuate the signals before they even emerge from the nozzle into the freestream. The waveguiding tubes each have a slot 525a, 525b that allows a predetermined small fraction of the energy within each tube to leak intentionally along a vee path to the reference reflector and then be received in the other tube through a similar slot. The transducers, when installed in their respective transducer ports and operated at wavelengths just a small submultiple of the transducer aperture, e.g., 25, 50 or 100 kHz, approximately, for apertures about 15 to 30 mm, lead to sufficient beamspread to obtain the reference information using the vee path illustrated, and to also obtain flow information along the vee path shown in broken fashion in the duct 2f 1f. The schematic of the waveforms associated with this type of reference and freestream interrogations represents the important reference and flow echoes at A and B, in the simplified waveform sketch below the drawing.

Figure 16:
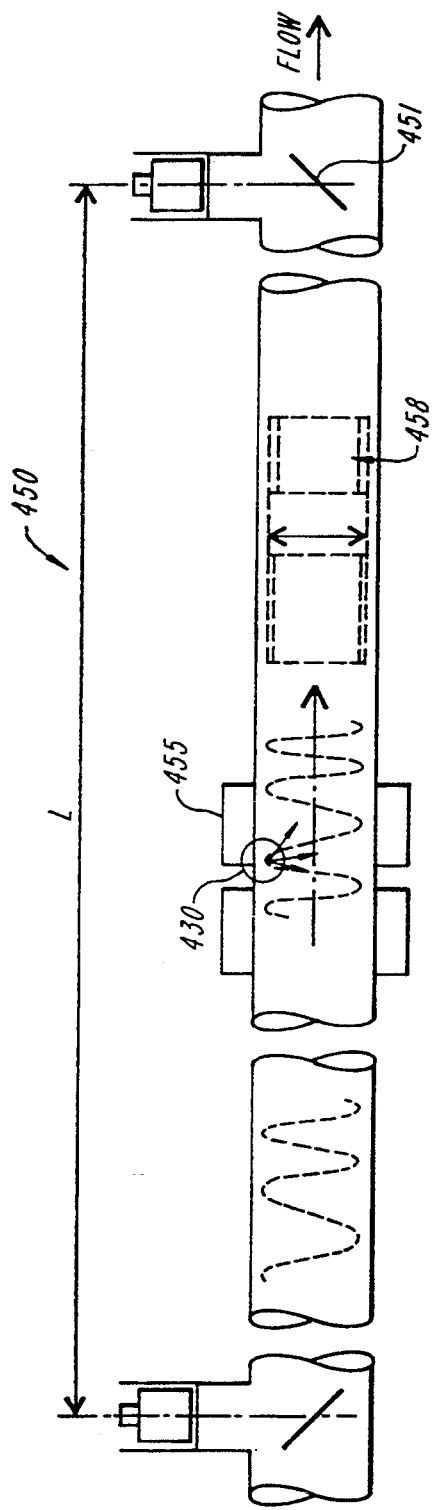
FIG. 16 illustrates signal isolation in a long, thin-walled flow cell of small diameter.

Returning now briefly to the first discussed isolation structure, that of alternating masses, a further embodiment with variations is shown in FIG. 16. This system 450 involves a measuring path of length L with the signal path defined by reflector plates 451 to direct ultrasonic signals along the flow axis, with a plurality of massive collars 455 placed about the conduit, and/or thick sleeves 458 placed within the conduit. The sleeves may be of differing thickness, hence inner diameter, in order to better break up reflections from the interior of the duct. A spiral coil 430, which may be of constant, progressive or irregular pitch scatters in the conduit wall any energy reflected against the wall from the fluid, so that an essentially purely axial wave propagates in the fluid. This arrangement effectively filters or sharpens the signal trace by eliminating higher modes and spurious multi-path vibrations traveling with the ultrasonic signal but not propagating axially.

While the above descriptions have focused on the isolation achieved between the ends of a vessel or conduit on the one hand, or a transducer and its surrounding vessel or conduit on the other hand, the described isolation structures may also be applied to free-standing, externally-attached or unconfined transducers and measurement systems. In that case, a simple counterbored yoke or bracket 440 as shown in FIG. 15D may be mounted on a frame, rod, or existing structure such as a beam or culvert, to direct its signals into, or receive signals from, surrounding air.

One application of such point-like gas-exciting transducers is an ultrasonic anemometer 450, shown in FIGS. 17 and 17a. Three acoustically isolated transducers 451,452, 453 are held by a rigid, non-rotating frame 456 having a body which directs the transducers along three independent pathways a, b, c having x, y, and z components, to receiving transducers 451, 452, 453 positioned to sense the signal from its sending transducer, providing a readily derived contra-propagation transit time interval, or other measurement, from which wind direction or speed components are calculated. O-ring isolators are shown in the detailed view FIG. 17A of one pair of transducers. By arranging that pathways a, b and c differ sufficiently, all three pathways may be interrogated at once by paralleling their respective transducers. As wind gusts can be quite rapid, the fast response afforded by interrogating all three components of wind essentially simultaneously yields more meaningful results than if there were substantial delays or uncertainties in synchronization for wind components sensed seconds apart, i.e., not simultaneously.

One particular application of this gas transducer signal technology is the provision of closed path signal loops, with the path defined by one or more transducers and/or reflectors, to measure a physical quantity corresponding to a path integral of interest. FIGS. 18 and 18A show a face view and an edge view, respectively, of a pipe flange 500 incorporating isolated transducers such as the transducers 310 of FIG. 15D.

A pair of transducer mounting bores 505, 506 are formed in the flange 500 directed at angles to cross at a single opening 510 in the inner circumferential edge of the annular flange, which is illustratively sized to be clamped or bolted as a measurement collar in a ten inch steel pipe, either between flanged sections of pipe, or alternatively slid over a section of pipe with an opening or thinned wall formed in the pipe and aligned below the opening 510. The transducer path is aimed along a midradius path, tangent to an axially centered cylinder of radius one-half the pipe radius, so that the ultrasonic beam is reflected twice from the inner wall of the conduit, forming an inscribed equilateral triangle path between sending transducer 505 and receiving transducer 506. The signal path transit time, together with the known geometry of the flange, thus provides a closed loop path integral of V·ds on a three-leg path surrounding the pipe axis. This provides a direct measure of the circulation $\Gamma_z$ about the conduit axis. The two transducers are located adjacent each other in the solid flange. In the illustrated 10-inch flange, the circulation path is $L_c = 15 \times 1.732$ inches and the total gas path is approximately $P = L + 3.26$ inches. To prevent gas-borne crosstalk in an arrangement where the two ports join as one, one must use a sufficiently high ultrasonic frequency, or may thread or otherwise roughen or modify the ports at regions 510a, 510b from the idealized geometry presented for illustrative purposes so that scatter from the first angled port does not coherently get up into the adjacent second port by way of their common passageway.

Inasmuch as the calculation of $\Gamma_z$ for this path requires the evaluation of $c^2 \Delta t/2$, where c=sound speed, it is clear that the "Flowmeter" can calculate other characteristics of the fluid that depend on c. Temperature T is one such characteristic, since for a gas, T is proportional to $c^2$. For many liquids, T may be calculated as a linear function of the sound speed, T=Ac+B, where A and B are constants.

Figure 19:
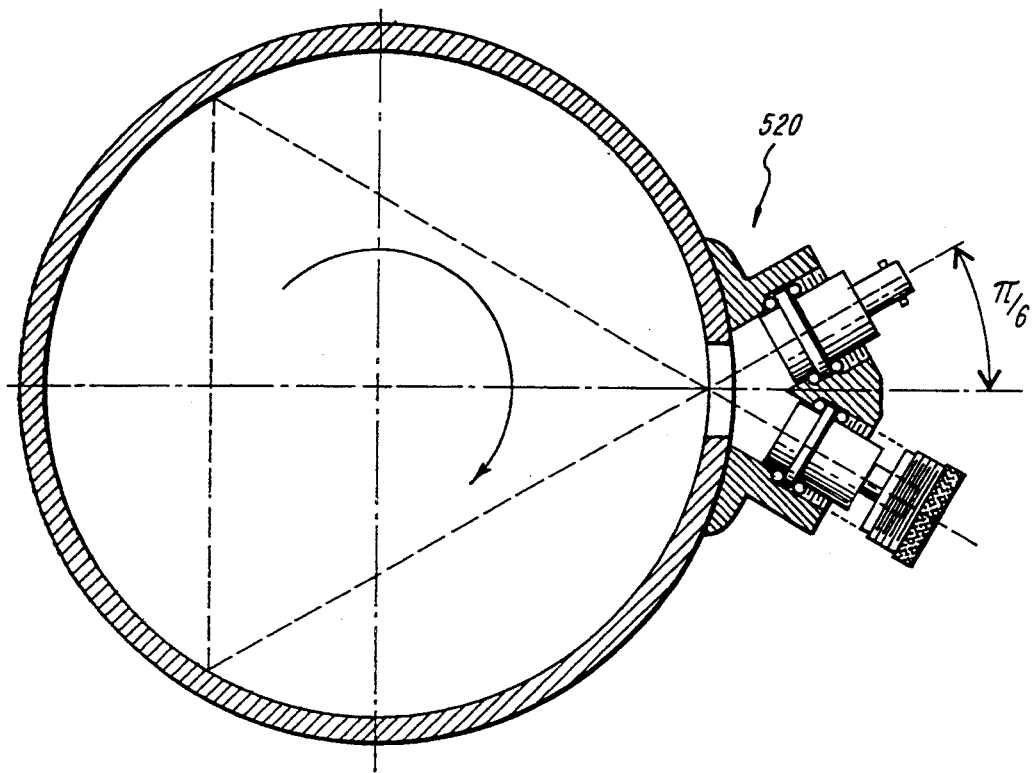
FIG. 19 illustrates another embodiment of a triple midradius circulation sensor.

FIG. 19 shows another embodiment of a device 520 for taking a midradius path measurement of circulation about the pipe axis. In this embodiment, a pair of isolated and angled transducers are mounted in an external block, directed along chordal paths through a pipe opening. By alternating propagation along clockwise and counterclockwise paths a measure of the magnitude of swirl or circulation $\Gamma_z$ about the axis is obtained.

In other applications, isolation transducers may be mounted with separate reflector elements or opposed transducers to define different closed paths, or approximately planar closed paths for determining particular characteristics or deriving other components of fluid circulation.

Figure 20:
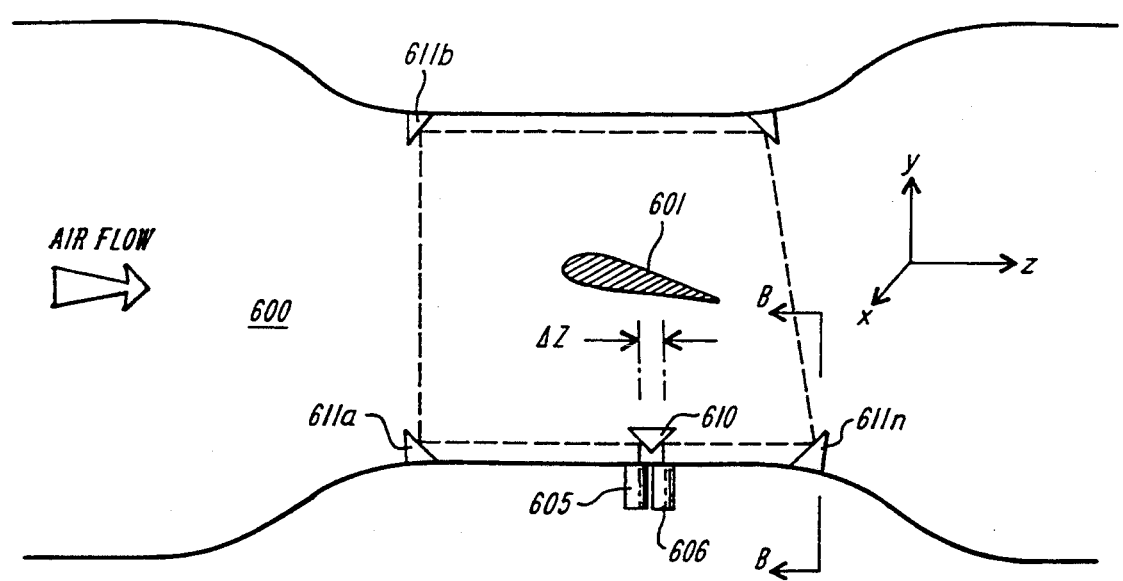

FIG. 20 shows another closed path sensor configuration 600, illustratively for sensing circulation $\Gamma_x$ about a test object 601 located in a wind tunnel. A pair of transducers 605, 606 are directed at a beam splitting reflector 610 (or a pair of single beam reflectors) that, together with reflectors 611a, 611b, ... 611n form a closed polygonal acoustic path around the object 601 between the two transducers. The transducer separation is selected to be small compared to the dimensions of the tunnel and the test object, so that the path is effectively a closed path. In lieu of the reflectors, separate transducers may define the endpoints of each segment, in which case more signal processing is required. The reflectors preferably are not located too close to the walls, in order to avoid transit time ambiguity and inaccuracy that might arise due to thermal or flow gradients in the boundary layer.

As shown in FIG. 20A, a pair of reflectors located in adjacent planes may be used instead of beam splitter 610 to define a full contour around the test object (so that $\Delta z = 0$). FIG. 20B is an end view, showing the vaned nature of the reflectors, which define measurement paths in closely adjacent planes while allowing normal airflow along the wind tunnel axis in the plane of interest.

In another embodiment shown in FIG. 21, by employing a spherical or cylindrical test chamber 550 which is smoothly enlarged from the nominal tunnel inlet and outlet, a single opening 555 (shown in detail in FIG. 21A) allows a triple midradius interrogation path using the chamber wall as a signal reflector. This provides a small number of paths, which are well centered in the air stream and require no protruding reflectors. As shown in FIG. 21A, the chamber opening may have a screen or mesh 556 along the interior wall contour to preserve smooth aerodynamic flow properties.

Figure 22:
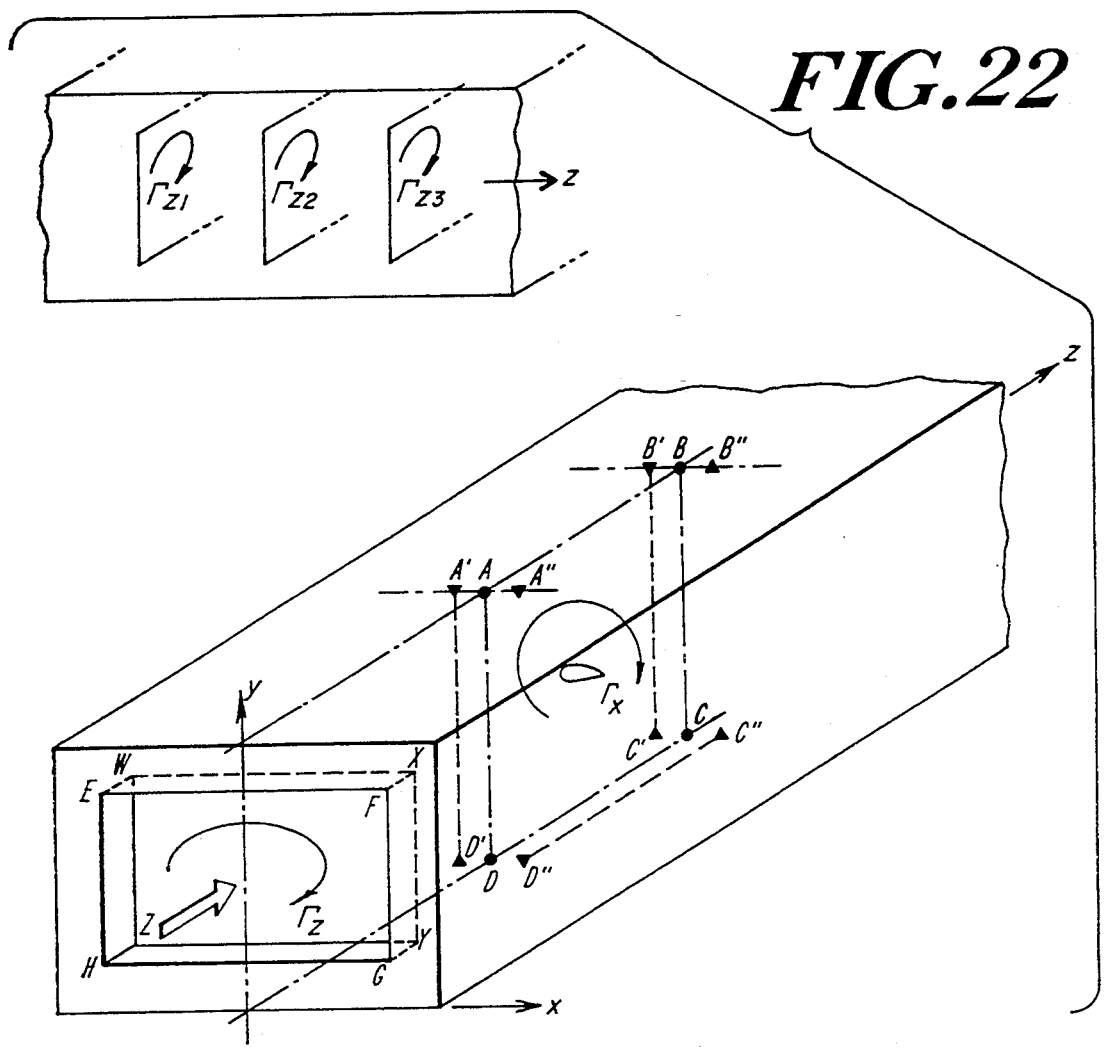
FIG. 22 illustrates closed path integration to measure aerodynamic quantities for an ultrasonic measurement of lift.

FIG. 22 illustrates in schema possible path integral measurements performed in this way. The circulation $\Gamma_x$ about a model extending in the x direction may be pieced together from path measurements made in parallel but slightly offset planes. For example, under reasonable assumptions of continuity, the integration path ABCD may be approximated with the segments A"B" and C"D" from one plane, and B'C' and D'A' from an adjacent plane, with both the "and' planes located adjacent to the plane of interest. This minimizes the aerodynamic effects of the transducers or reflectors on flow in the plane of interest.

Similar polygonal paths may be set up ahead of the test object to determine the swirl velocity at the inlet, and the circulation $\Gamma_z$ about the z axis. Thus, all functions necessary to compute lift may be directly measured by ultrasonic signal interrogation and simple signal processing. Since lift=$\rho V_z \Gamma_x$, and (a) the amplitude of the received signal yields the gas density $\rho$; (b) conventional contrapropagation measurements yield $V_z$; and (c) clockwise and counterclockwise path measurements yield $\Gamma_x$, the product of these three quantities yields the sought lift.

Referring still to FIG. 22, it will be understood that in order to utilize the primed and double primed planes that are close enough in proximity that measurements in these planes closely approximate the closed path integral required for a circulation measurement, one must be able to isolate closely spaced transducers such as those at A' and A", B' and B", etc.

Figure 22A:
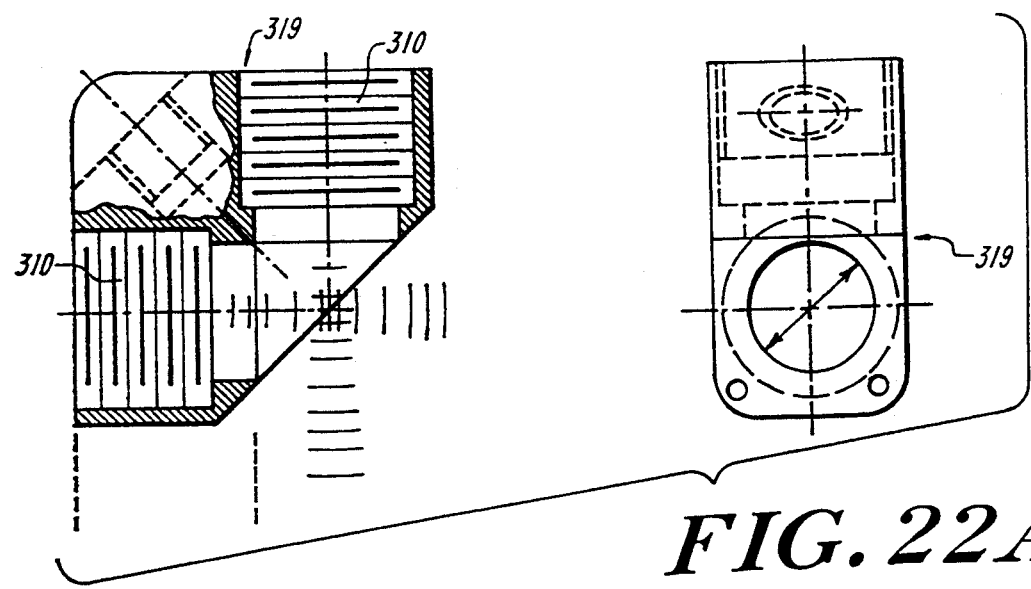
FIGS. 22A and 22B illustrate different transducer mounts.

An alternate approximation to the closed path integral can also be obtained using a corner transducer assembly as shown in FIG. 22A. In this design, a pair of transducers 310 are sealed and held in place with their axes both in one plane, using the O-ring flange sandwich method. The housing 319 for the two transducers is itself secured inside a wind tunnel, typically at four places in the yz plane to measure circulation about the x axis, that is, about a model oriented along the x axis. Each transducer is held as in FIG. 15.

Figure 22B:
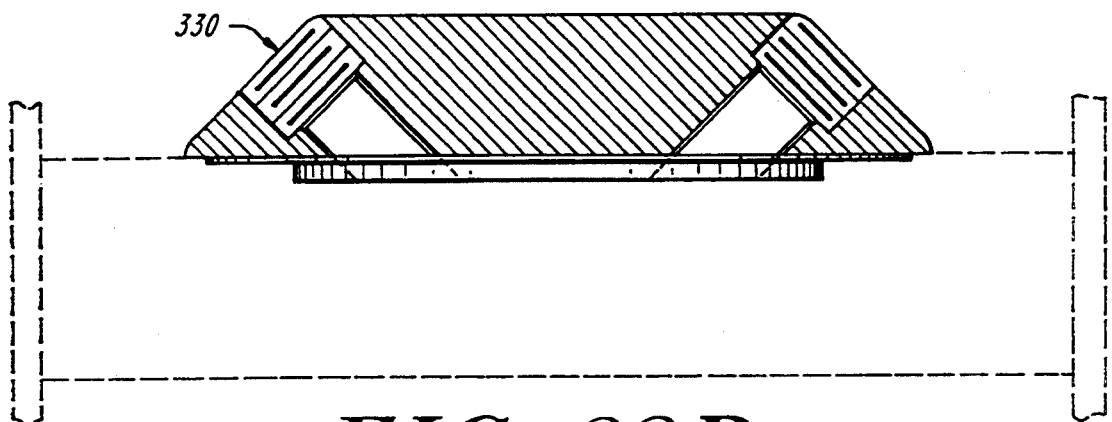

The ability to isolate by the O-ring flange sandwich method, two closely spaced transducers is also utilized in the blocklike housing 330 of FIG. 22B. This block is designed to be welded or otherwise sealably secured to a standard pipe.

The advantage of this block over prior art constructions is that the spacing of the transducers can be controlled more precisely than if one mounts separate angled coupling or nozzles onto the pipe. Precise control of spacing is retained even if the holes in the pipe are oversized, undersized or elongated, or have their axes normal to the pipe wall. Previously, the separate blocks were often selected as the standard design approach, in order to achieve isolation.

As one reduces the frequency f at which the flow or other gas characteristic is measured, there is generally more beam spread and a greater tendency for signals to propagate over spurious (unwanted) gas paths. The remedies for this problem include judicious use of scatterers on surfaces from which no reflection is wanted. The use of a spiral or inserted sleeve was mentioned earlier. Other remedies include anechoically roughening or corrugating portions of the offending surface, or threading the surface if it is cylindrical and conveniently threaded by tapping or inserting a "threadsert," which is a form of spiraled insert normally used to secure screws.

Figure 22C:
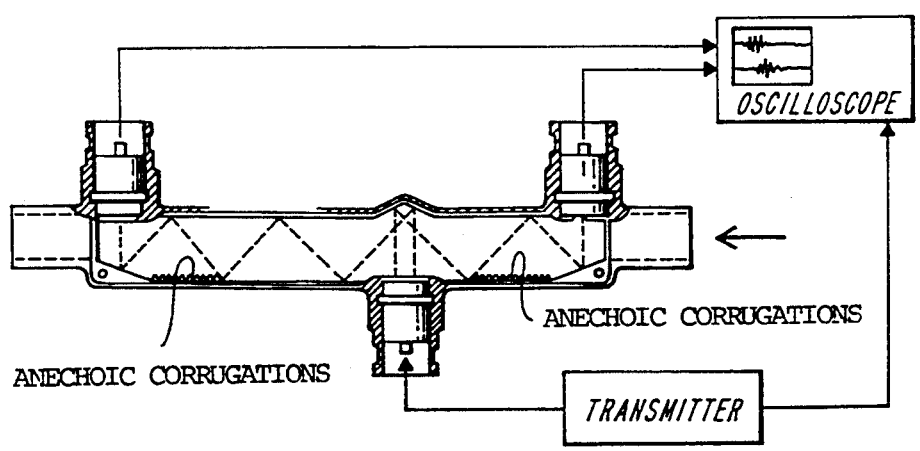
FIG. 22C shows an electrically paralleled differential path measurement system.

In the plastic square- or rectangularly-channeled flowcell of FIG. 22C, the plastic wall is periodically corrugated, as shown; so too is the cover plate (not shown). The two cell sections connected in series illustrates a configuration for switchless fast response flow metering, in which the system configuration greatly simplifies the required electronics.

The foregoing techniques of providing acoustic path isolation or, for longer pathways, temporal isolation of crosstalk allow one to implement systems wherein an ultrasonic driver/intervalometer measurement instrument dependably distinguishes the signals of interest.

In accordance with another aspect of the invention discussed above in relation to FIG. 15B, elements of a system are arranged so that plural transmitting and receiving transducers are connected parallel to a single channel of such an instrument, the signals being received in disjoint subintervals or timing windows so that transducer switching or multiplexing are not needed. Representative embodiments will be discussed in connection with multi-path sensing situations, such as wind-tunnel swirl measurements, triple midradius chordal measurements, axial- and cross-flow measurements, and the like.

Various differential-delay paths will be illustrated below, wherein the time interval windows for each path are spaced to avoid contributions in any window from transducer ringdown or path reverberations from a shorter path. In accordance with some embodiments of this aspect of the invention, the spacings of transducers are set so that received signals are centered in a sequence of windows at time intervals proportional to a sequence of prime numbers, thus avoiding a common factor which might allow interfering reverberations into a sampling interval. For example, in a four path Gaussian Quadrature flow cell, one may arrange to have each of the four path signals arrive in separate windows analogous to the four separate windows $W_1$, $W_2$, $W_3$ and $W_4$ of FIG. 15B. As a numerical example, for a 10-inch diameter steel pipe containing water, for which an appropriate interrogation frequency would be 1 MHz with a well-damped transducer that quiets down in a ringdown time $t_{rd}$=10 $\mu$s or less, i.e., ten cycles or less, the Gauss-Chebyshev paths could each lie in a different plane, such that $P_1$, the shortest path, in inches, would be the first prime number larger than 10 (that is, $P_1$=11 inches) and the other paths would have path lengths $P_2$=13 inches, $P_3$=17 inches and $P_4$=19 inches. At room temperature, the corresponding transit time would be $t_1$=176 $\mu$s, $t_2$=208 $\mu$s, $t_3$=272 $\mu$s and $t_4$=304 $\mu$s. As each of these "prime number paths" differ from one another by at least 2 inches, the transit time reception window centers are separated by over $3t_{rd}$ and no transit time $t_i$ is an integer multiple of any other time, by virtue of the prime number sequence. This substantially avoids overlap of transducer and other path reverberations.

Figure 1B:
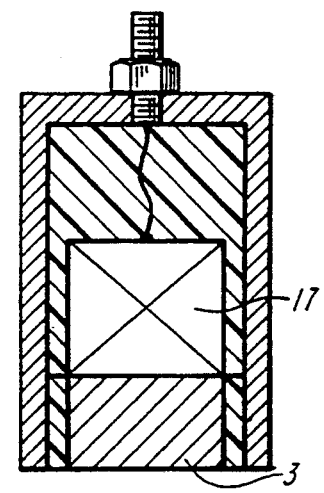

Gas transducers for use at lower frequency, e.g. 100 kHz or below, if made of rigid high-impedance crystals as shown in FIG. 1B, tend to ring on the order of 50 to 100 cycles even if damped by soft attenuative potting agents like silicone rubber. Thus, if the period $T_x$ of the transducer's natural frequency f is $T_x$=1/f=10 $\mu$s, the ringdown time $t_{rd}$ for 50 cycles of ringing is (50) (10 $\mu$s)=500 $\mu$s=(0.5) millisecond, and twice that, or 1 millisecond, for 100 cycles of ringing at f=100 kHz. Air paths corresponding to these transducer ringdown times are about 0.5 to 1 foot. Hence, a sequence of "prime number air paths" for transducers that ring for 100 cycles could be 3 feet, 5 feet, 7 feet, and 11 feet. Such ranges are within the practical capability of 100 kHz commercially-available ultrasonic equipment such as described, for example, by the applicant and colleagues at the EPRI Heat Rate Improvement Conference, November 1992. At f=50 kHz, there is less attenuation in air, so the range increases to over 50 feet, allowing one to employ an even greater number of prime number air paths, e.g., 13, 17, 19, 23, 29, . . . 47 feet. Any three of such prime number air paths may be used to define the spacing of transducer pairs for a three-component sonic anemometer having electrically-paralleled paths, as shown in FIG. 17.

Figure 17C:
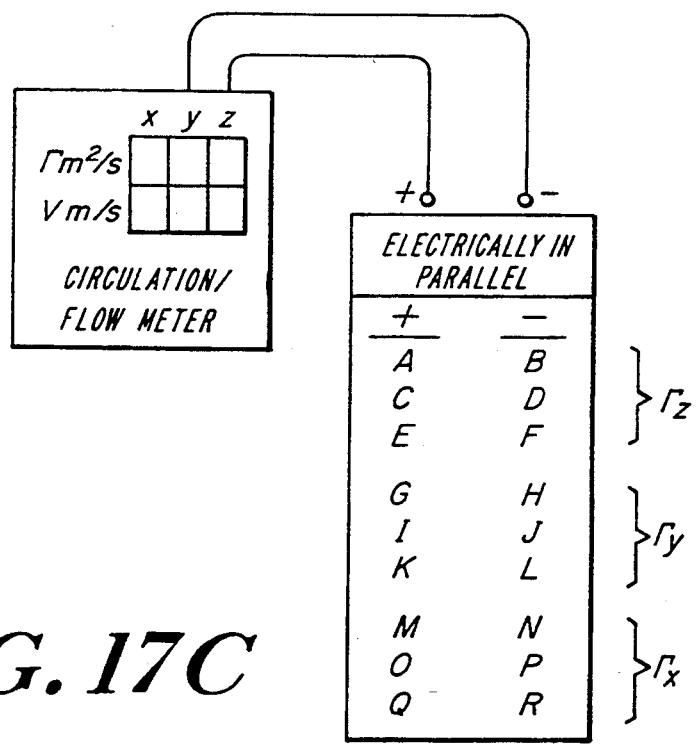
FIGS. 17B-17D illustrate details of a related system for measuring circulation and flow velocity components.
Figure 17B:
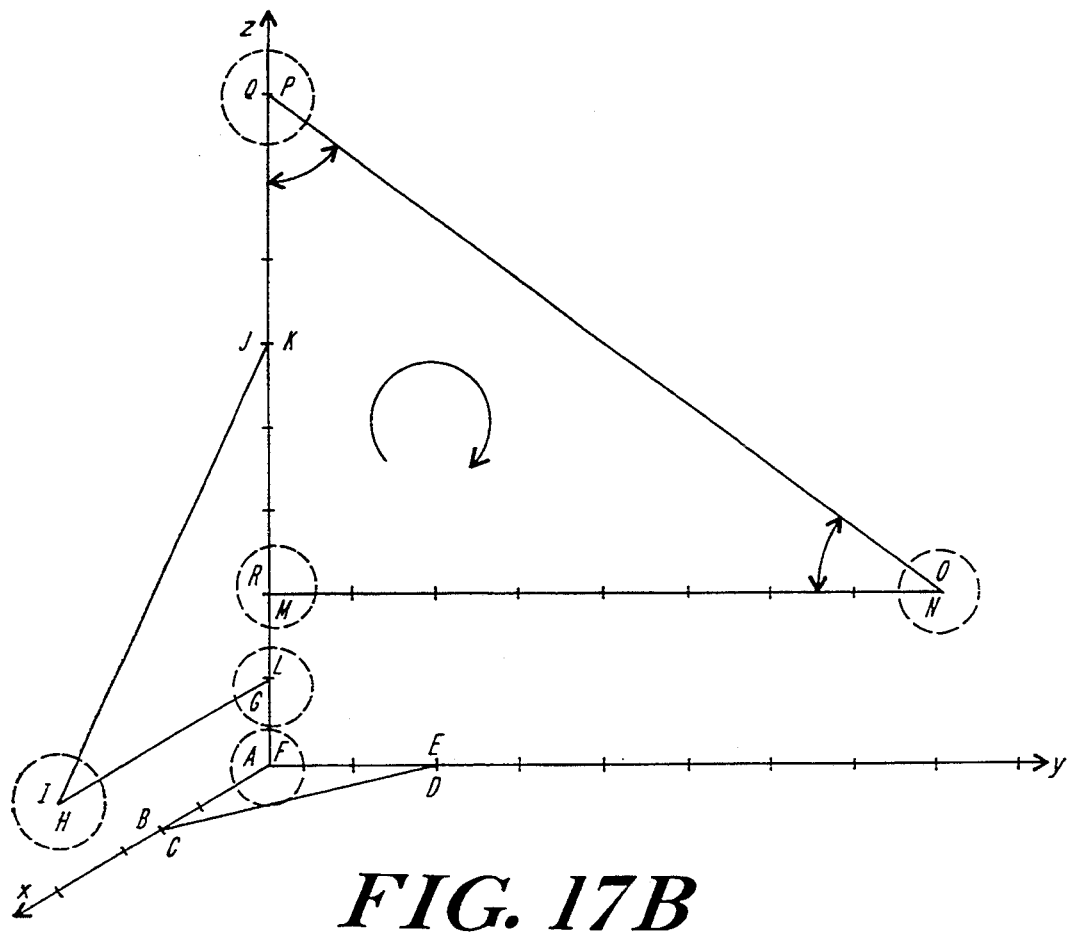
Figure 17D:
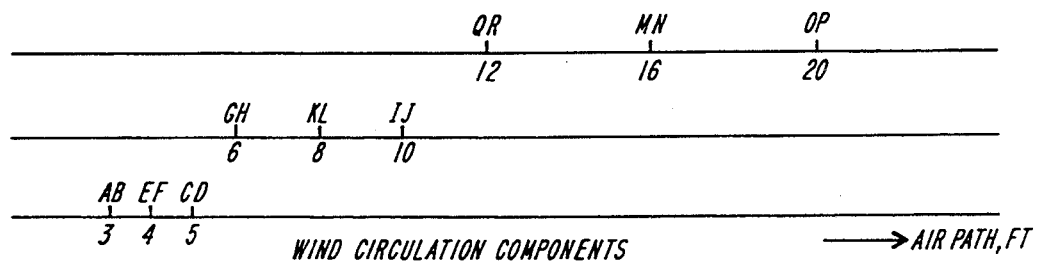

FIG. 17B shows such an arrangement of eighteen transducers mounted to perform substantially simultaneous acoustic interrogation along three independent closed loop signal paths with minimal processing instrumentation. Each contour is a right scalene triangle having 3-4-5 proportions, and each triangle is disposed in a different orthogonal plane and has its shortest leg longer than the hypotenuse of the next smaller triangle. A pair of transducers at each vertex of a triangle are aimed at the other two vertices of the triangle, so that the difference in transit time around the triangle is obtained from its six transducers, and represents the component of circulation $\Gamma_x$, $\Gamma_y$, or $\Gamma_z$ about the axis perpendicular to the plane of the triangle. FIG. 17C illustrates the channel allocation of the transducers A-R, which are connected as two sets of nine transducers in parallel to the driver/intervalometer. FIG. 17D plots the disjoint timing windows of the received path length signals. The illustrated configuration is for wind measuring swirlometer which requires only a thin frame to secure the transducers in the surrounding airstream. All hypotenuse paths are oriented differently (skewed), and in the open airstream reverberations should pose no problems, so it is not necessary to provide for "relatively prime" reception intervals of the type discussed above. The different x-, y-, and z- paths also yield $V_x$, $V_y$ and $V_z$ measurements. The invention also contemplates allocating a separate processing channel to each circulation measurement, with the same size frame and right scalene triangle used for each set of transducers, in a more compact embodiment.

In each of these embodiments, implementation of the invention contemplates the provision of well-aligned corner transducers, such as indicated schematically by the $\Gamma_y$ transducer pairs IH, GL and JK of FIG. 17B, which are preferably implemented in modular blocks, similar in construction to that of FIG. 22A, below, each having a pair of precisely-aligned bores for accommodating transducers directed along the bore axes. Advantageously, the blocks are either right-angle blocks, or else have their bores oriented at an angle such as thirty-seven, or fifty-three degrees, oriented precisely for either rectangular transducer arrays, or arrays laid out at one of the vertices of a 3-4-5 triangle. Alternatively, each corner block may comprise two blocks hinged together, each holding one transducer, so that their transmission angles may be adjusted in the field to a desired geometry and the block then clamped in that position. Thus, by arranging for temporally disjoint signal reception windows in this manner, a number of transducers may provide parallel inputs to a single processor, and achieve complex measurements.

By way of general further background, modern ultrasonic systems typically operate with a single instrument box of which the circuitry includes, on the one hand, a driver portion for energizing a transmitting transducer with a signal burst, and a digitally operated signal receiver/analysis portion which is synchronized to the drive burst and processes the signal received by a receiving transducer. Reference is made to commonly-owned U.S. Pat. No. 4,787,252 for a description of the digitally-implemented signal sampling, correlation and time- or frequency-domain analyses which may be effected by such instruments. For example, the receiver/processor may sample and digitize the voltage appearing across a receiving transducer several hundred times during a several millisecond measurement interval, may perform signal conditioning, and may determine transit time differentials, measures of signal quality and other system data. In prior art systems; a processing channel may be intermittently connected to several different receiving transducers by switching circuitry to make measurements on different pipes, or more usually a multichannel instrument has one processing channel connected to each receiving transducer. This may require the use of special interfaces and recording devices to combine or display the result of the separate measurements when they form parts of a single process, and typically this results in an inefficient use of the limited bandwidth of the highly specialized receiver/processor.

In accordance with a principal aspect of the present invention, receiving transducers are connected in parallel to a single processing channel, and plural received signals are processed by the digital analyzer in sampling intervals that are separated due to transmission path delays which are preferably greater than ring down characteristics of the sensors involved. This construction is especially useful for performing closed path circulation or swirl measurements, and measurements in a highly constrained environment, of the type shown in FIGS. 17B and 18-22, where differing length path legs may be selected to allow one instrument to measure all paths in sub-intervals of a single short time.

The instrument hence can acquire all the data necessary for it to compute flow and other fluid characteristics in a short time $T_c < n\ T_f$, where $T_f$ is the time of signal travel in the fluid, and n is less than ten, and preferably between one and three. The processor may complete its processing activity in under one millisecond, so for the various sensing configurations described, all signal acquisition and processing is essentially completed within one millisecond of the time it takes for the acoustic signal to propagate along the longest sensing path. Shorter path signals preferably are processed earlier. Thus, all measurements are performed within an interval substantially equal to or shorter than the longest transit time. The electrically paralleled construction is also useful in other flow measurements, such as the device of FIG. 22C, wherein the long multiply-reflected path results in separate arrival times at the two receivers due to differential retardation of the signal. Other embodiments are discussed below wherein reflected, scattered or delayed signals arriving at different intervals provide enhanced measurements.

Returning briefly to the system shown in FIG. 22 for measuring swirl and circulation, the closed contours ABCD or EFGH may be any closed paths in the YZ or XY planes, respectively. Preferably, however, they are arranged so that the paths AB, CD are different lengths than BC, DA, by an amount such that the transit time difference for waves simultaneously launched at one corner, is greater than the signal sampling interval of the receiving circuit, and such that the transit time along the shortest path (say BC) is greater than the ringdown time of a transducer interrogating that path.

With this constraint on path length, both transducers of a corner transducer FIG. 22A, or separate pairs of sending and receiving transducers at one corner, may be simultaneously actuated while a single channel receiver processes the signal received at two adjacent corners. Applicant refers to such a measurement system as having a differential path and electrically parallel transducers. As compared to conventional systems, such configuration dispenses with complex multiplexing or synchronization circuitry, and uses the internal measurement software defined processing intervals and sample definition. As discussed more fully below, this configuration reduces required measurement channels.

Rather than a closed path integral as illustrated in FIGS. 17B, 18, 21 and 22, a good measure of swirl may be obtained by interrogating a chordal segment in both clockwise and counterclockwise directions and then scaling the time difference $\Delta t$ to approximate the swirl. The circulation of a fluid flowing along a conduit, given by the closed integral of V·ds is approximated by $1.5 c^2 \Delta t$, where $\Delta t$ is the time difference of signal propagation in two opposing directions along a chord which is near to a midradius chord.

As with the other embodiments, these approximations may be performed at different stations along a flow, or in separate conduits at the same time, by using electrically paralleled differential path configurations. These configurations are useful for slower soundspeed interrogations, in which adequate temporal separation is achievable, such as in gases interrogated with wetted transducers. In such applications, single- or double-opening chordal interrogation may be performed using clamp-on transducer assemblies, as shown for example in FIG. 23.

Figure 23:
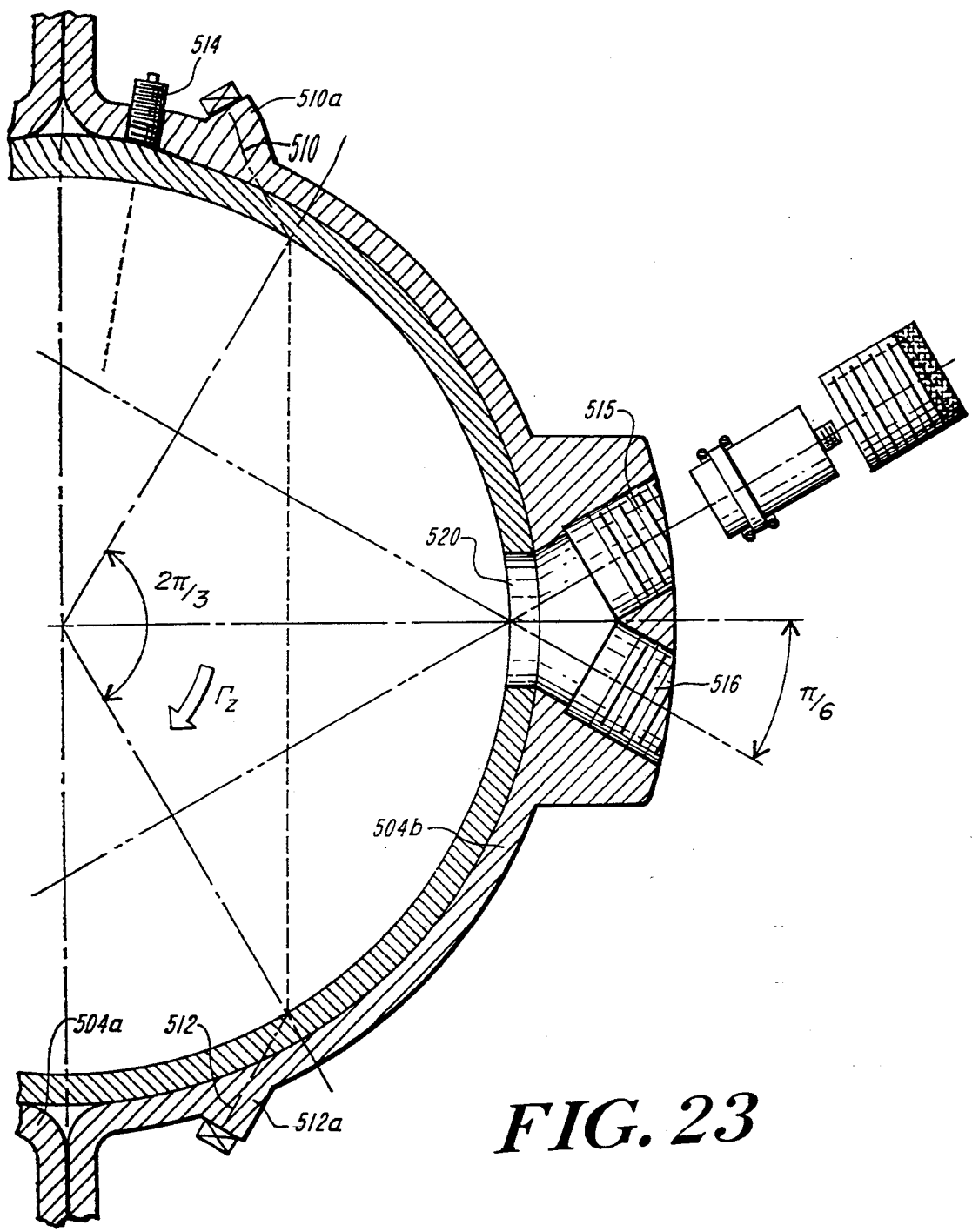
FIG. 23 and FIGS. 23A-23C show clamp-on chordal measurement systems.

FIG. 23 shows a cross-section through a large pipe or conduit 501 in a sensing system 500 of this type. A multipiece clamp assembly 504a, 504b, such as is commonly used as a wrought pipe clamp or extension pipe or riser clamp, is modified to have transducer mounts formed thereon, or more precisely welded to blocks thereon or clamped thereto in the positions indicated. A first pair of two transducers 510a, 512a attach to wedges 510, 512 welded to the clamp body. Both of these transducers are attached to the same half of the clamp 504b, and are oriented at an angle to launch and receive signals along a midradius chord through fluid flowing through the pipe. Their mounting angle is selected in accordance with the sound speed of the intended fluid, taking account of pipe diameter, wall thickness and refractive effects, as would be understood by a person skilled in the art. Another transducer 514 is shown mounted in the clamp at an angle for interrogating along a different path to an opposed transducer further along the axis of the pipe on the other side to take axial flow measurements. Finally, a pair of transducer mountings are shown 515, 516 angled over an opening 520 in the pipe and directed for taking closed path contrapropagation signal measurements using internal reflections from the pipe body, similar to the closed chordal path arrangement shown in FIG. 18, but in this case, the clamp is a simple strap metal clamp rather than a large precise casting or spool piece. Corresponding to opening 520 in the pipe is an oblong hole through the clamp. This hole may be threaded at its edges to eliminate any significant coherent scattering or crosstalk between the two closely spaced transducers 515, 516. In general, these latter two transducers and their closed path chordal interrogation are useful for gases, such as air.

The clamp assembly may be fitted with either these triple midradius chordal transducers, or with the clamp-on transducers 510, 512 suitable for interrogating liquids. As shown in the detail views included in this Figure, the clamp-on transducers attach to a wedge that extends through the clamp 504b and is pressed against the pipe wall to form acoustic contact as the clamp is tightened down. These rod wedges may also be wetted with a couplant.

Figure 23A:
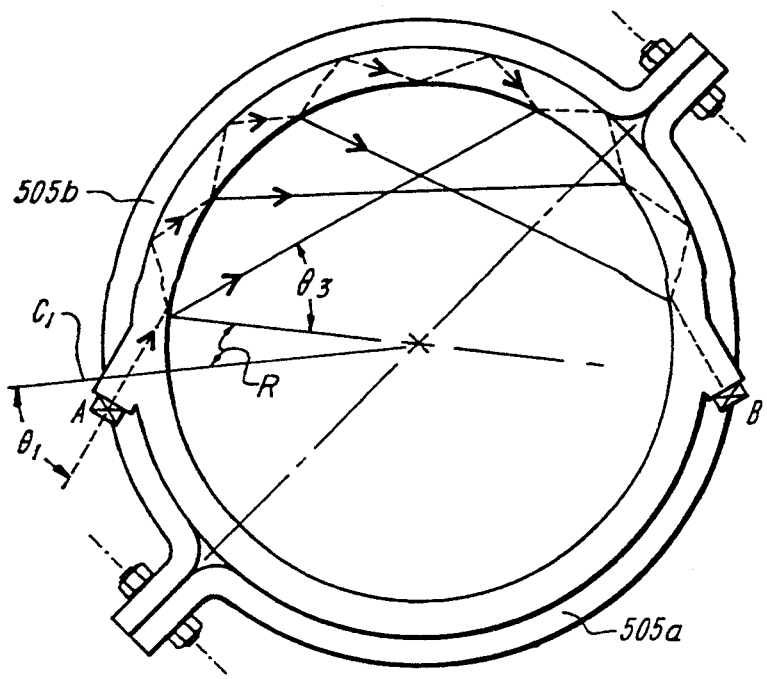

FIG. 23A shows a clamp-on swirl sensor variation of this system. In this embodiment, two pipe clamp halves 505a, 505b each have a wedge mounted thereon in a corresponding or identical position, so that when mounted together to fully surround the pipe, they lie at or near opposite ends of a diameter of the pipe. The wedge is oriented without particular regard to the liquid in the conduit, whose sound speed is $c_3$, so that wave energy launched by the wedge may internally refract, spread by diffraction and reflect numerous times within the wall of the pipe as shown in the Figures. It exits the conduit wall numerous times over a circumferentially-elongated region and proceeds to the opposite transducer. In this case, although the contrapropagation chords are not identical, the symmetry assures that the $\Delta t$ remains well defined and essentially the same for numerous chords and the positions of the sensors are thus not critical. This allows the system to be implemented by manufacturing clamp halves with a single transducer wedge mounting, despite application to liquids of differing $c_3$'s. Returning briefly to FIG. 23, it further bears note that in the gas measurement environment, leaking waves may propagate between transducers creating a certain degree of crosstalk, the amplitude of which will depend on the gas pressure. The strap may have a hollow section to accommodate such leakage and provide a gas path between transducers that can be independently monitored for noise level to determine operating pressure. Note that to detect the presence of swirl, it suffices to determine if $\Delta t$ is nonzero. Therefore, even if all chords do not yield identical $\Delta t$, the $\Delta t$'s will be of like sign and thus be additive if swirl is nonzero, allowing a simple and reliable determination of whether swirl is present.

Figure 23C:
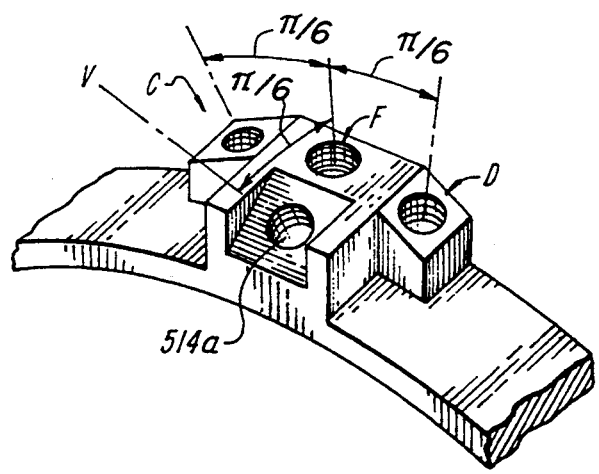
Figure 23B:
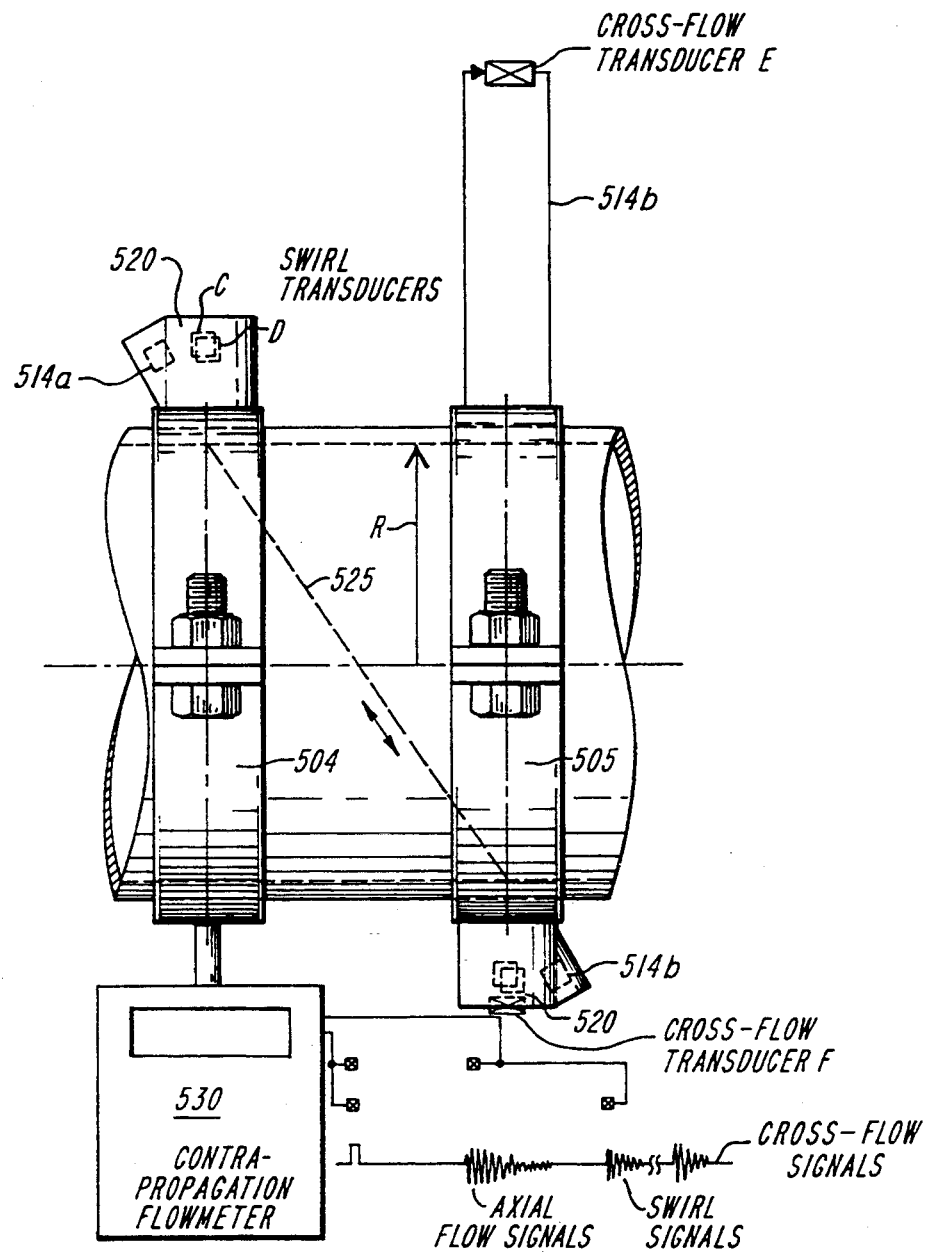
Figure 23D:
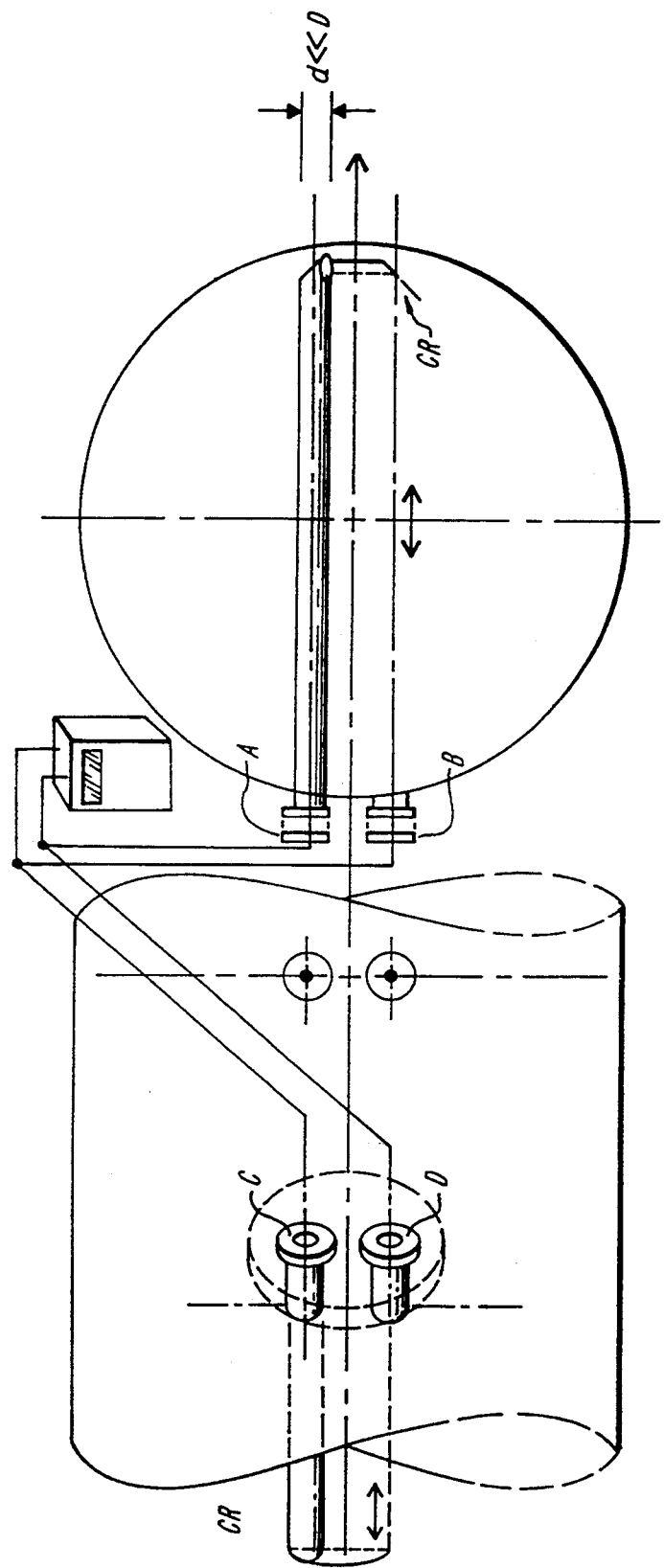
FIG. 23D illustrates a system with two clamp-on transducer assemblies which also takes axial and cross flow measurements.
Figure 23E:
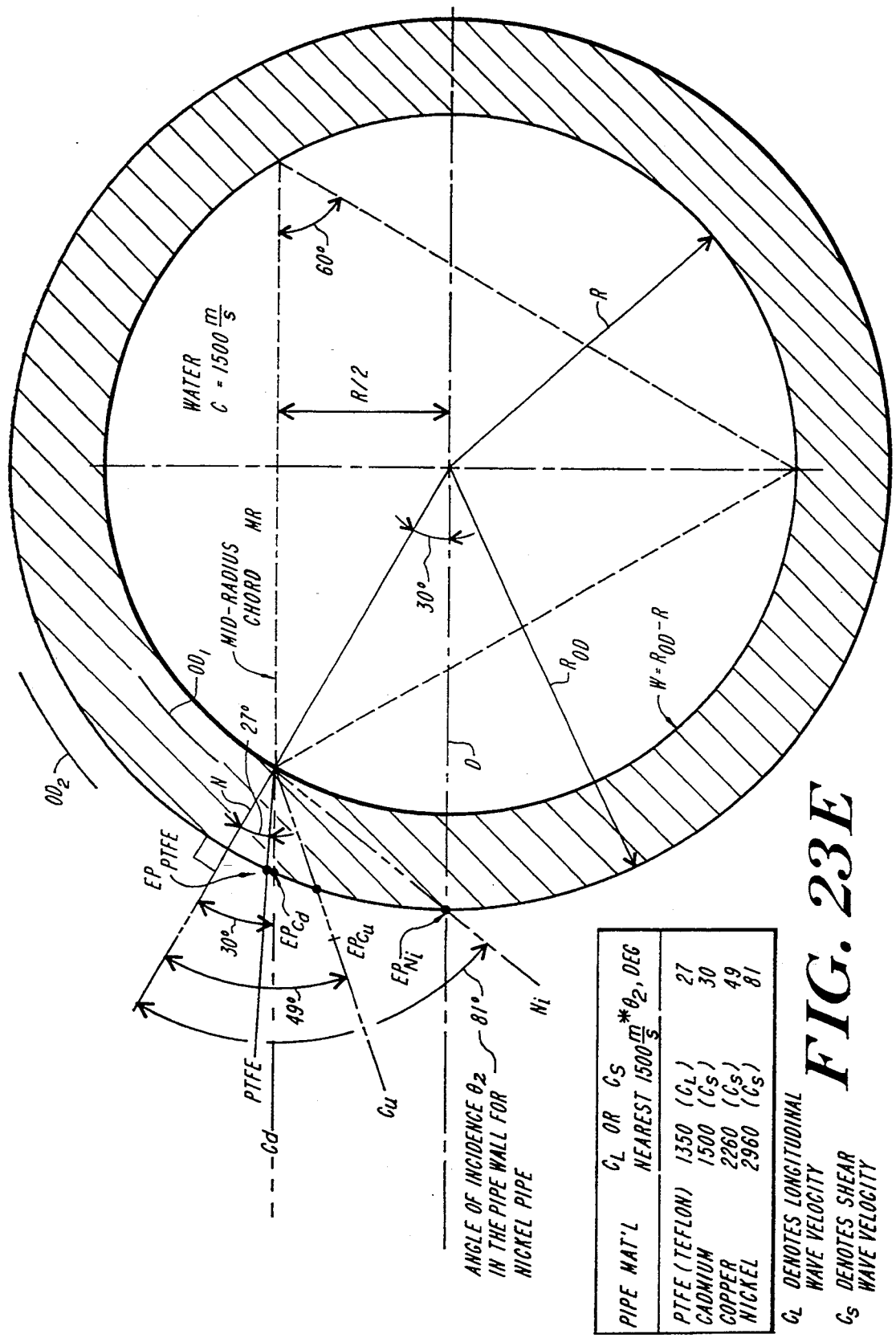
FIG. 23E illustrates chordal interrogation with external clamp-ons.

FIG. 23E shows several ways of theoretically achieving a swirl-sensing chord exactly along a midradius path. In this drawing, the pipe has an internal radius R, and external radius $R_{OD}$, and a wall thickness $w = R_{OD} - R$. The Figure is drawn with relative proportions for a medium-size conduit, and the locations of the outer surface (hence the wall thickness relative to diameter) for a large diameter or small diameter pipe are indicated by ghost lines OD1 and OD2, respectively. A midradius chord is designated MR, while the normal line at its intercept with the inner wall of the conduit is designated N. A pipe diameter D is parallel to the midradius chord MR. The pipe is presumed filled with water having a sound speed $c = 1500$ m/s. By way of examples, for pipe materials such as PTFE, Cd, Cu and Ni, having published sound speeds as listed in the table in that Figure, applicant has calculated angles of incidence $\theta_2$ in the pipe wall and location EP of the signal entry point that is necessary for each material in order to refract along the midradius chord parallel to the diameter and spaced therefrom by R/2. The location of each entry point on the pipe OD in that Figure, for the given pipe wall thickness w varies for each material. Note that for PTFE (Teflon), whose longitudinal wave velocity is less than that of water, the entry point is slightly above the midradius' extension at the pipe's outer surface. For Cd, whose $c_S$ equals c in water, 1500 m/s, the entry point is exactly on the extension of the midradius chord. For more common metals, such as Cu and Ni, the entry point is below the midradius extension, and for Ni it is exactly on the diameter D.

It will be appreciated that this entry on the diameter would appear to be a very special case, and the result would generally differ when considering a pipe of slightly larger or smaller OD, or a pipe of material having a different sound speed than 2960 m/s, or a pipe in which the liquid therein has a sound speed $\pm 1500$ m/s. However, the methodology for identifying transducer placement to effect interrogation along a desired chord is quite general, and similar remarks apply for chordal interrogations of swirl along chords other than the midradius. Based on this type of analysis, applicant concludes that the preferred entry point, for a horizontal chord to be interrogated both clockwise (CW) and counterclockwise (CCW), will typically be at least twice the pipe wall thickness below the swirl sensing chord, and may be up to about ten times the wall thickness below that chord. For typical steel, stainless steel and aluminum pipes containing water, Snell's Law will limit the swirl sensing chord to a position slightly closer to the center than the midradius chord. This leads to a rule of thumb, that the swirl sensing transducers be positioned 2 w to 12 w below the R/2 chordal intercept, for those combinations. A corollary rule of thumb found by applicant, is that if the first rule in combination with pipe dimensions happens to straddle the pipe diameter, then the diameter is a preferred entry point. This corollary rule of thumb recognizes the ease of coupling across the diameter at diametrically opposed points, using for example quick-acting clamps, and furthermore, the diametrically opposed points of entry for swirl sensing are also the preferred points of entry for sensing cross-flow. Hence, the same transducer block can accommodate both swirl and cross-flow sensing transducer piezoelements.

FIG. 23B shows a vertical elevation, partly in section taken parallel to the axis of the conduit shown in FIG. 23. In this embodiment, two strap assemblies 504, 505 are placed around the conduit, spaced apart along the axis of airflow, and arranged such that a slanted transducer 514a (similar in orientation to transducer 514 of FIG. 23 but in the present instance, tilted axially) is aimed along the axially slanted path 525 to a similar transducer 514b mounted obliquely on the other strap clamp 505. As illustrated, the oblique clamp-to-clamp transducer mountings are formed in large three-axis mounting blocks 520, each of which also has two chordally directed transducers C and D mounted like transducers 515, 516 in FIG. 23 to take chordal measurements along a closed path in the plane of the clamp. A single channel contrapropagation flow meter 530 is attached to the transducers. Illustratively, designating clamp transducer 514a as transducer A and 514b as transducer B, the flow meter may be attached to transmit simultaneously in parallel on transducers A and C and process the signals received from transducers B and D. The oblique path 525 is set at 30 degrees from the vertical, making the path length 2.3 times the radius. The sum of the three midradius chordal paths between transducers C and D is approximately 5.2 times the radius, assuring that the single channel receives signals from transducers B and D in separate time intervals, differing by a time greater than the ring down time of the transducers. Transmission and reception are switched in ping-pong fashion yielding an upstream/downstream difference giving the flow velocity and a clockwise/counterclockwise difference giving the vortex circulation in the conduit.

In FIG. 23B, the right-hand strap is also fitted with a vertically-extending buffer tube 514b at the top of which is depicted a first cross-flow transducer E. Cross-flow transducer E communicates across the diameter to second cross-flow transducer F mounted in the lower block 520. For air cross-flow measurements at ordinary pressures, it is necessary to make a hole through the strap and pipe wall so that the ultrasonic beam from transducer E can efficiently enter the air within the pipe. Contrapropagation measurements from E to F and then from F back to E yield the cross-flow velocity $V_x$. The buffer tube 514b is made along enough so that the cross-flow interrogation signals arrive long enough after the swirl signals as illustrated in FIG. 23B, or between the axial and swirl signals, ringdown permitting.

FIG. 23C shows a detailed view of the three-axis mounting blocks 520 of FIG. 23B, with threaded bores for the transducers C, D and 514a of that Figure. Transducers C and D are offset $\pm \pi/6$ from the normal in a plane perpendicular to the pipe axis, while transducer 514a mounts in a bore directed $\pi/6$ across that plane along the axial direction.

The tapped hole centered on the normal n in FIG. 23C accommodates one of the cross-flow transducers, namely cross-flow transducer F shown in FIG. 23B. This transducer communicates through the same hole in the pipe as do the swirl and axial flow transducers. For a corresponding system for liquid application, where simple clamp-on interrogation is practical, the cross-flow transducers would be clamped normal to the pipe on opposite sides. In the clamp-on case, a preferred clamp-on wedge design provides in one module both swirl-sensing and cross-flow sensing piezoelements. However, pipe diameter, material and wall thickness will sometimes preclude a practical combination of swirl sensing and cross-flow sensing in one small module owing to lack of a path length solution that would yield disjoint reception windows as discussed above.

Another method of measuring cross flow is illustrated in a schematic end view, FIG. 23D, showing a conduit wherein sending and receiving transducers A,B are mounted next to each other on the same side of the conduit and oriented along parallel paths. A small diameter (e.g., one- or two-inch) pipe much smaller than the conduit diameter serves as a stagnation waveguide to carry the signal between a corner reflector CR and one of the transducers so that the signal traveling between transducers A and B will be delayed differently in each direction when there is cross flow. This configuration allows cross flow to be sensed from a single side of the conduit. A similar corner reflector arrangement with a stagnation waveguide in one leg is shown in a pair of transducers C,D mounted on flanges oriented at 45° to the flow axis. In each case, both transducers of the pair might also be mounted on a single larger flange unit.

Figure 24:
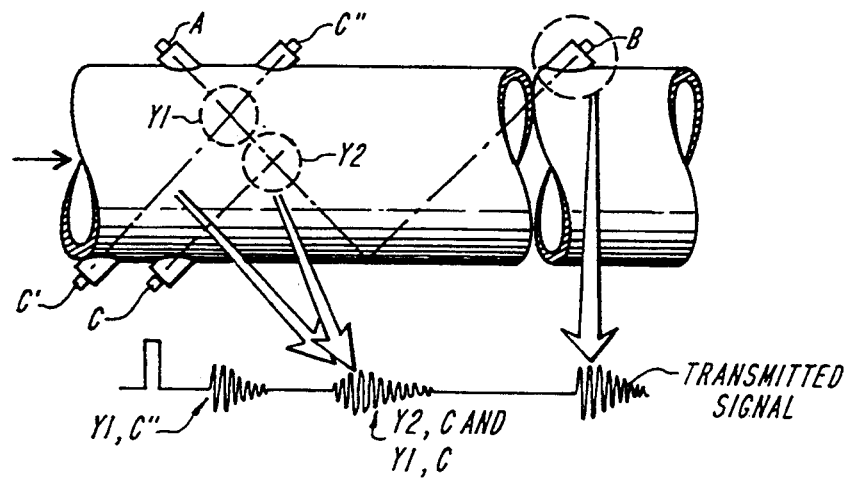
FIG. 24 illustrates another temporally separated acoustic system.

Other arrangements of transducers and different sensing systems are possible. FIG. 24 shows an arrangement wherein three transducers A, B, C are located along a conduit, with transducers A and B located on the same side of the conduit to receive signals reflected specularly and coherently from the opposite wall, while transducer C is located across from A but well away from the center of its transmission lobe to receive transmitted energy predominantly from scatterers in the flowstream located in scattering cell Y2. Thus, the transmission and reflection paths are all on one pipe, but sufficiently different to allow electrically paralleling of the B and C transducer outputs into a single processing unit without external switching.

In FIG. 24, a scattering cell Y1 is drawn near the midradius location, such that backscatter is received at transducer C' and forward scatter at transducer C'', at arrival times approximately the same for C and C' but much earlier for transducer C''. A transmission/reception signal trace appears below the Figure. If C' and C'' are the only receivers connected in parallel, the scatter shown in the time line as Y1, C' will be responsive primarily to axial flow, and relatively insensitive to cross-flow, whereas the scatter received by C'' (the earlier arrival) is primarily responsive to cross-flow and relatively insensitive to axial flow. In other words, backscatter responds to axial flow and forward scatter to cross-flow, for the geometry illustrated. A scattering cell such as Y2 on or near the axis can be made appropriate for separating axial from cross-flow in the manner just described if one arranges that the arrival times for forward and backscatter are sufficiently well separated by more than the ringdown from anywhere in the scattering cell. One solution is to be sure that the two receivers that are in parallel are not symmetrically disposed about the scattering cell, that is, the two scatterer receivers are spaced different distances from the scattering cell, differing by more than the ringdown time $t_{rd}$, and furthermore, one is forward of the scattering cell, and the other behind it, forward and behind being reckoned with respect to the direction of axial flow, represented in FIG. 24 by the arrow at the left side of the pipe.

Figure 25:
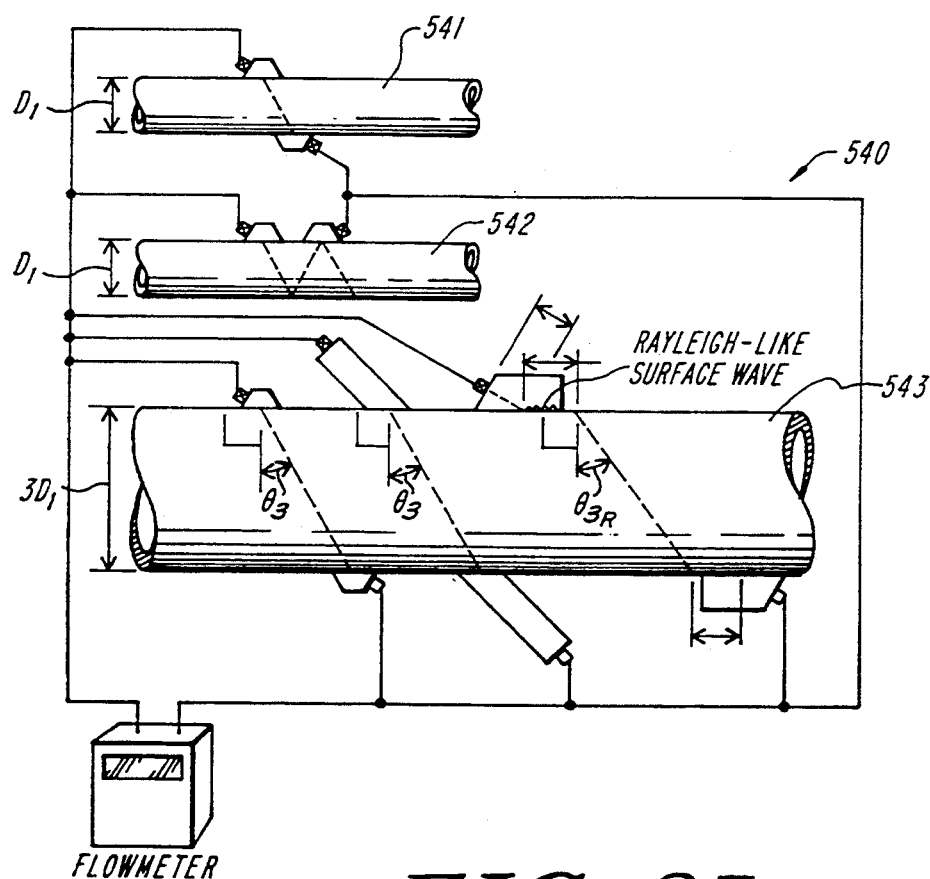
FIG. 25 illustrates a multiconduit system with many measurements electrically paralleled.

More complex constructions are possible, or variations in which different pipes are interrogated but the transducers are wired together in parallel to utilize a common signal processor or flowmeter. FIG. 25 shows one such system 540. This system includes three pipes 541, 542 and 543, each of which is illustrated with a different configuration of transducers interrogating it. Conduit 541 has a small diameter D1 and has a sending and a receiving transducer located diagonally opposite each other for direct transmission through fluid in the pipe. One transducer is connected to the transmission side of the flowmeter, the other to the receiving line. It will be understood that these lines are preferably switched within the meter itself to ultimately send and receive on each transducer for developing contrapropagation measurements. Conduit 542 is an identically sized pipe, however the transducers are arranged on the same side of the conduit to receive and send signals along a path approximately twice as long defined by reflection from the inside wall of the conduit.

Figure 25A:
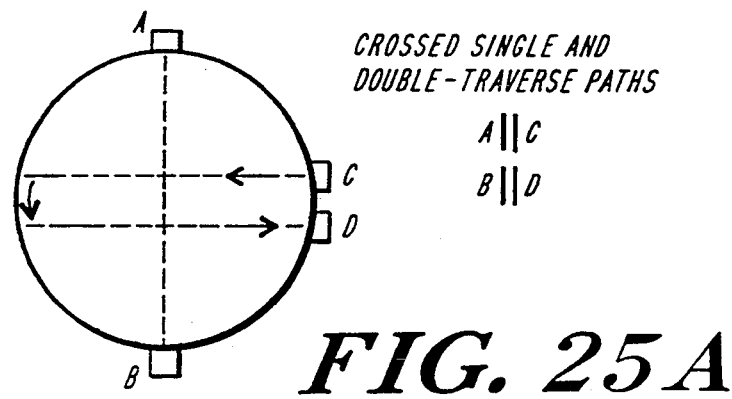
FIG. 25A illustrates a single conduit measurement system with paralleled axial and cross flow measurements.

FIG. 25A shows an end view of pipe 541 representing crossed single- and double-traverse paths, with transducer A electrically wired in parallel with C and B in parallel with D. This is equivalent to the paralleling of transducers shown for pipe 541 and identical pipe 542, but now the crossed paths are utilized to detect asymmetry in the flow profile, so as to obtain a more accurate measure of flow. This is another instance of multipath interrogation in one pipe to improve accuracy or reduce uncertainty associated with the flow profile.

In FIG. 25, another transducer is shown in phantom on the bottom of pipe 542, to indicate the classical configuration of opposed transducers with a three-leg reflected path between them. However a transducer is not used at this location, because a double-reflected, triple-traverse, path in the first pipe 541 would create substantial interference with such a signal which is displaced only slightly in the flow direction. Finally, the third conduit 543 is shown much larger than either of the other two. In this conduit, three pairs of transducers are illustrated which viewed from the leftmost to the rightmost pair illustrates different techniques for having the signal arrive in a spatially distinct time window so as to be processed on the same channel as the transducers from pipes 541 and 542. In the leftmost pair of sending and receiving transmitters, the transmitter is mounted with an appropriate wedge for directly transmitting from one transducer to the receiving transducer across the pipe of diameter 3D1. In the next one, the transducers are mounted via buffer rods to introduce a time lag between signal transmission and the signal entry into the conduit and fluid. This allows an even longer time separation for this second set of transducers. In the third (rightmost) pair of transducers, the transducers are mounted in a wedge angled to launch Rayleigh-like surface waves into the wall of the pipe which then radiates into the fluid and they are received along a path slightly offset from the end of the transducer mounting wedge. This propagation through the wedge and conduit wall offers an additional range of delays for temporally separating the signals of the different transducers.

In all of the foregoing cases, the transmission occurs at the same instant in the transmitting transducer, while the delay interval to reception varies, allowing a single channel to process all received signals for the six different measurements. Each of these transit time variations is introduced in a clamp-on transducer assembly, allowing great flexibility in the overall configuration of systems. In general, the reception times may be adjusted by arranging differences in the diameter of the conduit, the angle of incidence, the type of wave traveling in the pipe wall ( as has been extensively discussed above in connection with flexural wave transmission), the number of traverses, the difference in sound speed in the liquid, and the incident path length (e.g. short wedge or long buffer). In addition, the conduit may be deformed to change the path length in the liquid.

Pipes 541 and 542 may be taken to represent supply and return lines of equal cross-section of fuel, hydraulic fluid on an aircraft, or a cooling water supply and drain combination. In other words, the same liquid composition exists in both pipes. In this situation, the sound speed c in the liquid may be an accurate indicator of the instantaneous average temperature T in each of the interrogated segments, and hence of the density of the liquid in each pipe, and in particular, the difference in densities. By measuring both the flow velocity V and the sound speed c simultaneously in supply and return lines, one can obtain a fast-response measure of mass leakage. Note that in the absence of a density correction, a difference in V might merely be due to a temperature rise, and not at all due to a leak. Conversely, a temperature rise, if uncompensated, could mask a leak, as the V's might be the same in both conduits despite different mass flow rates.

If the fluid is compressible, such as a gas, determination of mass flowrate depends not only on V and T, but also on the pressure P. Gas pressure in principle is derivable from the amplitude of the gas borne signal, provided all attenuation effects and other non-pressure effects have been eliminated. Another method of obtaining fluid pressure, independent of pressure dependent transmission in the fluid, will be described below in connection with FIG. 29.

Figure 27:
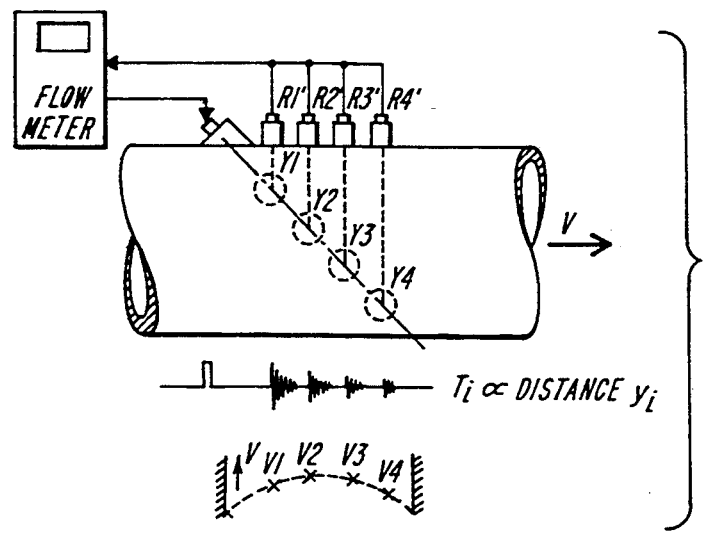

FIG. 27 shows a flow measurement system wherein a plurality of scatterers, Y1, Y2, Y3, Y4 are positioned at different stations across the diameter of a conduit along a path from a transmitting transducer T. Each reflector reflects signals to a receiving transducer R1', R2', R3', R4', all of which are connected in parallel to the processor section of a flowmeter. This provides a succession of increasingly long paths to the successive receivers so that each signal is received in a distinct time interval identified with one of the scatterers $Y_i$. Taking the flow velocity V to be zero at the walls, a smooth flow profile is constructed and the pipe contents can be represented as the velocity at each station times the annular area of a ring about that station to provide a total mass flow rate for the conduit. In such a calculation, one would average the velocities obtained in scattering cells or stations symmetrically disposed about the axis. In very large pipes and/or in very attenuating fluids, it may not be practical to obtain scatter from stations beyond the centerline. In that case, one can obtain both forward and backscatter time-separated scatter signals, if one wants to quantify the axial and cross-flow components, as discussed previously.

Figure 26:
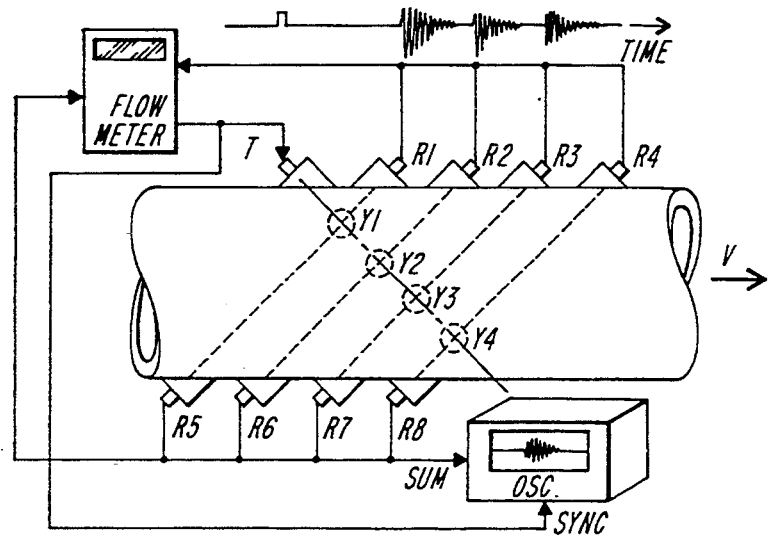
FIGS. 26 and 27 show systems using a multiplicity of scatter path signals.

FIG. 26 shows a somewhat related embodiment wherein additional receiving transducers R5, R6, R7, R8 are located on the opposite side of the conduit. Each scatterer $Y_i$ thus can provide a forward and a backscattered signal. However, note that the path T-Y1-R5 equals path T-Y2-R6, etc. Hence, paralleling R5-R8 tends to generate one composite scatter signal all in one window, as represented by the illustrated receive signal burst on the oscilloscope trace. This arrangement does not distinguish scatter from Y1, Y2, etc. To time-separate the signals, one cannot simply use any arrangement. One suitable time-separating arrangement is shown by the receivers R1-R4 at the top of this pipe, analogous to those on top of the pipe in FIG. 27.

The idea of electrically paralleling isopaustic (same time delay) paths is not new. Examples of this idea appear in applicant's 1989 book, using pairs of parallel midradius chords. The problem with that isopaustically paralleled method, is that paths get weighted unintentionally in proportion to the electromechanical conversion efficiencies of the transducers used for each path. As all transducers cannot be manufactured identically, or one transducer may age or otherwise deteriorate differently from those used in other paths, the results in all paths will be affected when the signals are added or paralleled.

By time-separating the signals from each path in accordance with the present invention, the isopaustic problem is avoided.

There may, however, be compromise situations where it will be acceptable to parallel different pairs of isopaustic paths. For example, consider a Gauss-Chebyshev four-path spoolpiece which is to be manufactured subject to the constraints of minimizing the overall axial and radial lengths. This latter constraint could make it impractical to find four sufficiently different path lengths, but it may be possible to find only two different path lengths. Thus, one solution is to parallel electrically all four paths, but setting up the inboard pair and outboard pair to provide substantially isopaustic delays, differing from one another by the ringdown time. This preserves the fast-response characteristic of multiple paths in parallel, and still allows the electronics to distinguish inboard from outboard path signals.

FIG. 28 shows another embodiment wherein flow is measured simultaneously along two separate conduits using a single channel flow meter. In this case, the interrogating transducers A, B for one conduit are spaced apart a different path length than the transducers C, D for the second conduit, and the transmission signals are initiated simultaneously so that transmitters and receivers both operate in parallel. In FIG. 29, the transit time is adjusted by providing a different buffer path length from one transducer to a reflector located in the flow line. This approach allows a great range of adjustment so that separate conduits may readily be set up to operate in separate time intervals. Similarly, as shown in FIG. 30, different conduits containing entirely distinct materials with different sound speeds may be interrogated in parallel with the slower sound speed delaying one signal to a separate time interval.

Figure 30:
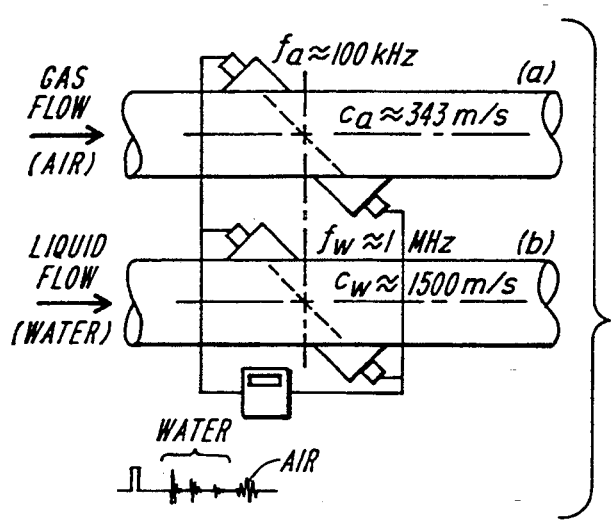
FIG. 30 illustrates a complex system with different fluids in different conduits.

In FIG. 30, the air path is long enough to allow enough time for the water transducer to ringdown and also to allow time for triple, quintuple, etc. reverberation paths in the water to die down.

FIG. 29A shows an enlarged view of a transducer for use with fluids, liquids or gases but especially important when gas pressure $P_g$ needs to be measured. It differs from the gas transducer of FIG. 1B in several important respects. Within this transducer of FIG. 29A, a solid path is included, having a transit time much less than the gas path transit time of path $P_{29}$ in FIG. 29. The solid path in FIG. 29A includes a smooth unbonded dry interface 291 which may be self-aligning as illustrated by the wedge and channel shape shown in FIG. 29B or, as illustrated in FIG. 29A, mating parts may be mutually aligned by an acoustically-isolated or non-transmissive sleeve 292. Part of the acoustic energy generated in piezoelement 293 when energized via electrical connector 295a, travels to the right and is pressure-coupled across interface 291 by an amount that depends on, and which is approximately proportional to, the gas pressure $P_g$. The greater the pressure $P_g$, the greater is the pressure signal amplitude $S_p$ appearing at electrical connector 295 connected electrically to the second piezoelement 294. One can arrange to put multiple interfaces like interface 291 in series, which increases sensitivity to $P_g$ but at the undesirable expense of increasing complexity. Although the phenomenon of pressure coupling of ultrasonic waves is well known, examples being cited in applicant's 1989 book, applicant believes the use of pressure-coupling within a fluid-interrogating transducer assembly as illustrated in FIG. 29A to measure gas pressure $P_g$ is novel. Furthermore, applicant is not aware of any published account showing the importance of making the pressure-sensing path that includes one or more pressure-coupled interfaces very short compared to the fluid path interrogated by transducers electrically-paralleled with transducers 293 and 294.

Figure 31:
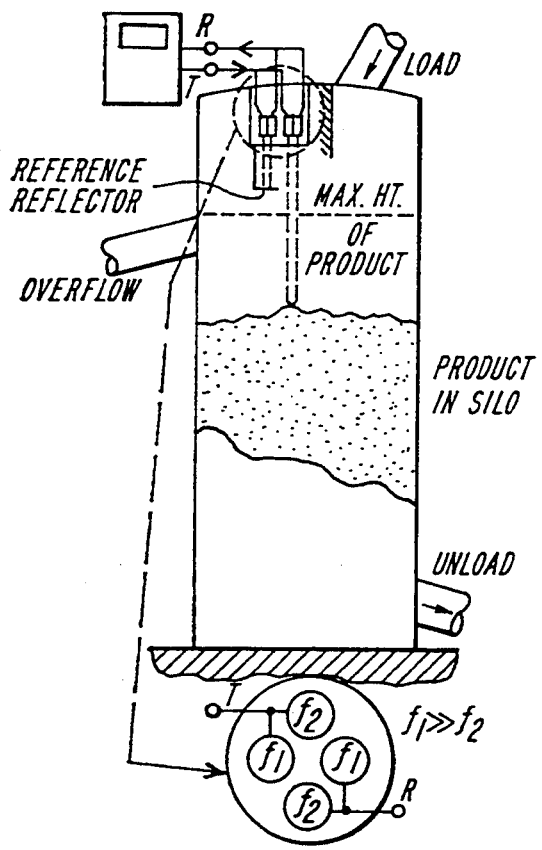
FIG. 31 illustrates a fill-monitoring system for material in a hopper or storage tower.

While not strictly speaking a fluid, a flow of powdered material or such into a silo may be monitored by an overhead arrangement of transducers as shown in FIG. 31, wherein a first pair of transducers are directed laterally at an overflow opening in the side of the silo, while a second pair are directed vertically to send and receive acoustic signals bounced off the top of the accumulated product in the silo. While the product may slump and pile irregularly and thus be a poor reflector, the minimal transit time does provide an indication of the maximum height achieved and the occlusion of an opening for the overflow path at the side of the silo provides an abrupt and distinct change in both path length and quality of the reflection seen by the second pair of transducers. Since the vertical path and oblique path are also of different lengths, these two pairs of sending and receiving transducers may be connected to a single transmitter/receiver to operate as a height gage for the possibly non-reflective granular or powdered material in the silo. A reference reflector in the upper assembly placed close to the transducers may provide an initial return signal that serves as a timing reference, an overfill threshold for path length evaluation, or serves for setting an amplifier gain control.

Figure 32:
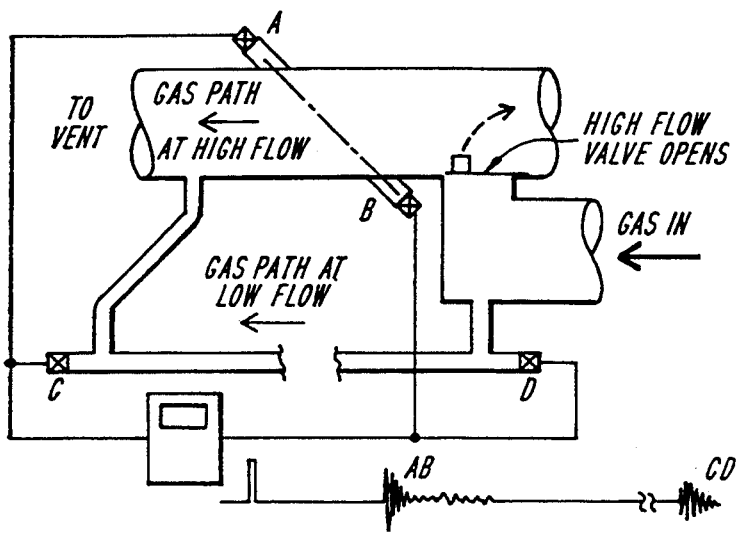
FIG. 32 illustrates an electrically paralleled system for simultaneously monitoring a flow cell and a bypass path.

FIG. 32 shows yet another embodiment of a single channel device performing plural measurements in parallel. In this embodiment, a primary gas flow passes through a lower flow cell where transducers C and D interrogate the normal low flow path along an axial path through a small diameter conduit. Under conditions of greater flow, a flap or check-valve opens into a larger conduit where transducers A and B interrogate the flow across the conduit. Both sets of transducers are connected to a single instrument and the path lengths are arranged to provide reception signals in different windows when the transmission occurs simultaneously.

Figure 33:
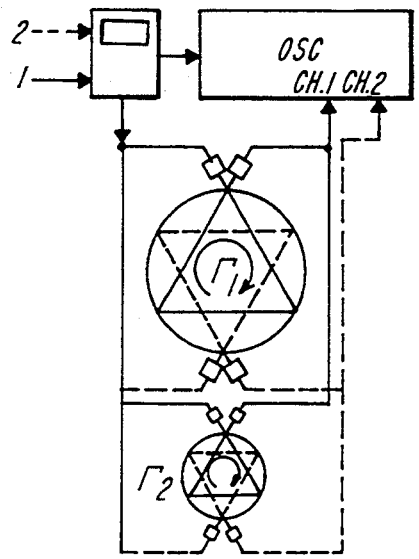
FIG. 33 shows a circulation measurement system.

FIG. 33 shows schematically a further arrangement wherein circulation or swirl measurements are taken along two separate conduits, or along two different size contours, or with two separate pairs of transducers taking clockwise and counterclockwise measurement in each conduit. Such arrangements may be useful in situations where the circulation must be measured at different places along the line of flow, or where substantially simultaneous clockwise and counterclockwise measurements at a single station along the pipe are required for each pipe. In this case, a two channel instrument is used, still showing a great economy over conventional circulation measurement systems.

Figure 34A:
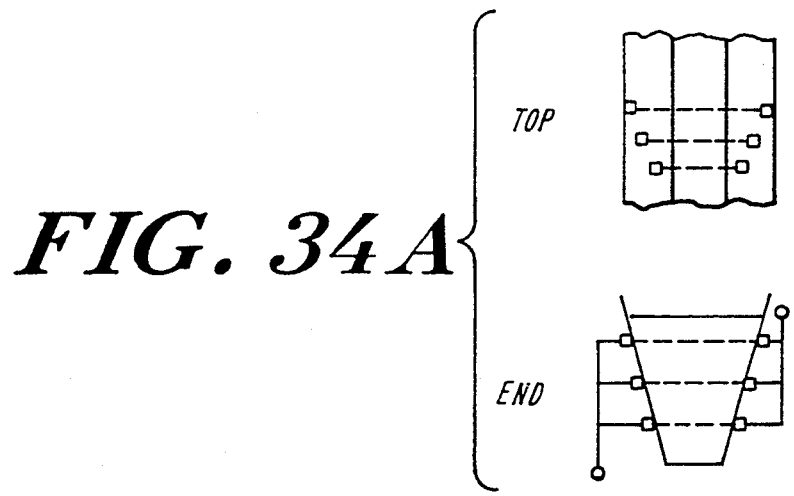
FIGS. 34A, 34B show arrangements for electrically paralleled measurements on rectilinear and prismatic, respectively, conduits or vessels.

FIG. 34A shows a top and end view of transducer arrangements on a tapered trough or hopper in which measurements of liquid presence, liquid flow or other liquid characteristics are performed simultaneously at different stations along the height of the conduit.

Figure 34B:
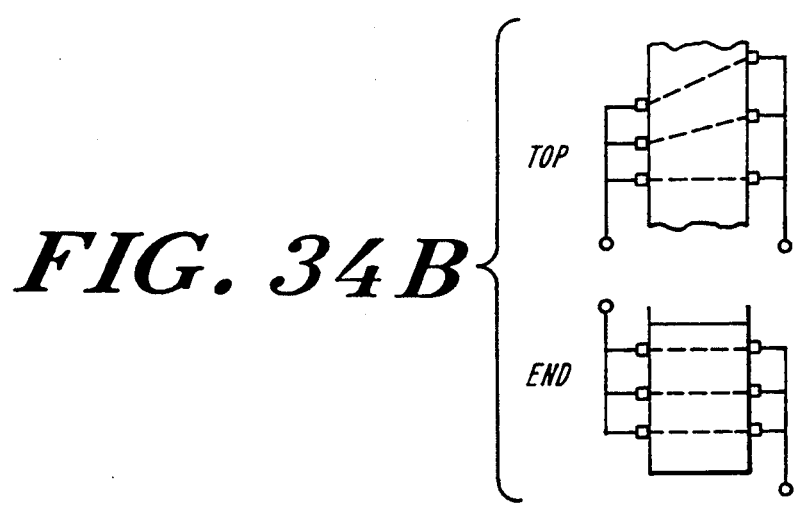

FIG. 34B shows similar top and end views for a rectangular channel. In this case, pairs of sending and receiving transducers are arranged at successively greater skew angles to obtain a sufficient path length differential for separation of the received signals.

This completes a description of the principles of the invention, together with illustrative embodiments and several preferred constructions for diverse transducer isolation and gas or other fluid sensing applications. The invention being thus disclosed, variations and modifications thereof will occur to those skilled in the art, and such variations and modifications are included within the scope of the invention to which an exclusive right is asserted, as defined by the claims appended hereto.

What is claimed is:

1. A fluid measurement system comprising
a single channel measurement device having transmission means for producing a transmission signal to actuate an acoustic transducer to propagate signal energy and also having a single channel signal reception means for receiving and processing electrical signals from an acoustic transducer that receives the signal energy,
means defining a region containing a fluid to be measured by propagation of said signal energy, and
means mounting a plurality of transducers for acoustic interrogation of fluid in said region, said means mounting at least two of said plurality of transducers as receiving transducers in receiving paths for receiving such signal energy at separate and non-interfering time intervals when said measurement device produces a single transmission signal, such that the signal energy received by said receiving transducers is processed by said single channel reception means to perform fluid measurement.

2. A fluid measurement system according to claim 1, wherein said mounting means includes clamp-on transducer mountings.

3. A fluid measurement system according to claim 1, wherein the transducers in receiving paths include transducers located on a plurality of separate conduits.

4. A measurement system according to claim 1, wherein the transducers in receiving paths perform at least two different measurements selected from among axial flow, cross-flow, pressure, temperature, liquid level and circulation measurements.

5. A measurement system according to claim 1, wherein the transducers in receiving paths include at least first and second transducers that receive acoustic energy that is primarily reflected off fixed targets and primarily scattered from scatterers moving with the fluid, respectively.

6. A fluid measurement system according to claim 1, wherein signal transit times along said paths are approximately proportional to a sequence of prime numbers.

7. A fluid measurement system according to claim 1, wherein the sequence of prime numbers are consecutive primes.

8. A fluid measurement system according to claim 1, which is a gas measurement system interrogated by acoustic waves of period P, and wherein said receiving paths determine adjacent time intervals that are separated by an interval of at least 50 P.

9. A fluid measurement system according to claim 1, wherein the receiving transducers sense at least two of axial flow, cross-flow and swirl from the same transmission.

10. A fluid measurement system according to claim 1, wherein receiving transducers are located forward and back of each other in relation to a scattering cell to receive acoustic energy from a single transmitting transducer as acoustic energy is scattered by the scattering cell, for determining both axial flow and cross-flow.

11. A fluid measurement system according to claim 1, wherein said mounting means includes clamp-on mounting means.

12. A fluid measurement system according to claim 11, wherein the mounting means includes at least two axially-separated strap-mounted transducer assemblies.

13. A fluid measurement system according to claim 1, wherein said mounting means includes an open frame that holds transducers directed along acoustic paths in at least two different planes for measuring characteristics of an unconstrained fluid.

14. A fluid measurement system according to claim 11, wherein the clamp-on mounting means mounts in a plane, and orients a first transducer to direct acoustic energy in said plane, and a second transducer to direct acoustic energy transverse to said plane.

15. A fluid measurement system according to claim 1, wherein the device completes processing of said signals within a time interval substantially equal to transit time of said acoustic interrogation.

16. A fluid measurement system comprising
    a single channel measurement device for actuating an acoustic transducer and processing electrical signals from an acoustic transducer,
    means defining a fluid containment for containing a fluid to be measured, and
    means mounting a plurality of transducers for acoustic interrogation of the fluid, said means mounting at least two of said transducers in receiving paths for receiving energy at separate and non-interfering time intervals from simultaneously actuated acoustic transducers wherein one of said transducers includes a transducer assembly having a housing, a transmitting transducer mounted in the housing for transmitting a signal through the fluid, a reference receiving transducer in the housing, and material coupling the transmitting and reference receiving transducers to each other, the material varying its transmission characteristics in accordance with fluid pressure applied thereto, said material providing a short acoustic path such that the reference receiving transducer receives a signal representative of fluid pressure in an initial time interval before receiving a signal transmitted through the fluid.

* * * * *